United States Patent [19]

Miller et al.

[11] Patent Number: 5,591,746
[45] Date of Patent: Jan. 7, 1997

[54] TREATMENT OF DAMAGE FROM A STROKE USING 4-AMINO(4-METHYLPIPERAZIN-1-YL)-5-(2,3,5-TRICHLOROPHENYL)PYRIMIDINE

[76] Inventors: Alistair A. Miller; Malcolm S. Nobbs; Richard M. Hyde; Michael J. Leach, all of Langley Court, Beckenham, Kent, England

[21] Appl. No.: 470,948

[22] Filed: Jun. 6, 1995

Related U.S. Application Data

[62] Division of Ser. No. 444,963, Dec. 4, 1989, abandoned.

[30] Foreign Application Priority Data

Dec. 7, 1988 [GB] United Kingdom ............... 8828620
Apr. 14, 1989 [GB] United Kingdom ............... 8908561
Aug. 18, 1989 [GB] United Kingdom ............... 8918893

[51] Int. Cl.⁶ ............................................. A61K 31/505
[52] U.S. Cl. .................................... 514/255; 544/325
[58] Field of Search ......................... 514/255; 544/325

[56] References Cited

U.S. PATENT DOCUMENTS

| | | | |
|---|---|---|---|
| 3,940,393 | 2/1976 | Greenspan et al. | 424/251 |
| 3,980,781 | 9/1976 | Snell et al. | 424/251 |
| 4,005,203 | 1/1977 | Stickney et al. | 424/251 |
| 4,005,204 | 1/1977 | Stickney et al. | 424/251 |
| 4,006,235 | 2/1977 | Stickney et al. | 514/275 |
| 4,535,080 | 8/1985 | Audiau et al. | 514/255 |
| 4,542,136 | 9/1985 | Carminati et al. | 514/252 |
| 4,613,603 | 9/1986 | Biziere et al. | 514/242 |
| 4,624,952 | 11/1986 | Biziere et al. | 514/252 |
| 4,725,600 | 2/1988 | Takaya et al. | 514/269 |
| 5,136,080 | 8/1992 | Miller et al. | 558/410 |

FOREIGN PATENT DOCUMENTS

| | | |
|---|---|---|
| 0021121 | 1/1981 | European Pat. Off. . |
| 0063509 | 10/1982 | European Pat. Off. . |
| 0114770 | 8/1984 | European Pat. Off. . |
| 0115713 | 8/1984 | European Pat. Off. . |
| 0169139 | 1/1986 | European Pat. Off. . |
| 0238905 | 9/1987 | European Pat. Off. . |
| 0330468 | 8/1989 | European Pat. Off. . |
| 0330469 | 8/1989 | European Pat. Off. . |
| 0382636 | 8/1990 | European Pat. Off. . |
| 0379806 | 8/1990 | European Pat. Off. . |
| 3620841A1 | 12/1987 | Germany . |
| 727151 | 3/1955 | United Kingdom . |
| WO92/02513 | 2/1992 | WIPO . |

OTHER PUBLICATIONS

Welt et al, AACR Abstracts, 1983, #588, "Phase II Chemotherapy of Pancreatic Adenocarcinoma With Metoprine (DDMP) 2,4–Diamino–5–(3'4'di–chlorophenyl)– 6–methyl–pyrimidine", Clinical Investigations.

Welt et al, AACR Abstracts, 1983, #589, "Metoprine Therapy of Advanced Sarcomas in Previously Untreated Adults", Clinical Investigations.

Magill et al, ASCO Abstracts, 1982, # C–88, "Phase II Trials of Metoprine (DDMP) in Pretreated Adults with Advanced Soft Tissue Sarcomas", Clinical Pharmacology.

Cavallito et al, "Lipid–Soluble Inhibitors of Dihydrofolate Reductase 1. Kinetics, Tissue Distribution, and Extent of Metabolism of Pyrimethamine, Metoprine, and Etoprine in the Rat, Dog, and Man", vol. 6, No. 3, pp. 329–337, Drug Metabolism and Disposition.

Currie et al, "Phase I Trial of Metoprine in Patients With Advanced Cancer", Cancer Treatment Reports, vol. 64, No. 8–9, Aug./Sep. 1980, pp. 951–956.

Duch, "Elevation of Brain Histamine Levels by Diaminopyrimidine Inhibitors of Histamine N–methyl Transferase", Biochemical Pharamacology, vol. 27, pp. 1507–1509, Pergamon Press Limited 1978, printed in Great Britain.

Duch et al, "Histamine: Elevation of Brain Levels by Inhibition of Histamine N–Methyl Transferase", Copyright 1979 by Elsevier North Holland, Inc., pp. 287–295.

Georges et al, "Structural and Electronic Properties of Anticonvulsant Drugs: Substituted 3–Tertiary–amino–6–aryl–Pyridazines, –1,2,4–Triazines and –Pyrimidines", J. Chem. Soc. Perkin Trans. II, 1989, pp. 449–455.

Hamrell, "Inhibition of Dihydrofolate Reductase and Cell Growth by Antifolates in a Methotrexate–Resistant Cell Line", Oncology 41: 343–348 (1984).

Hough et al, "Inhibition of Brain Histamine Metabolism by Metoprine", Biochemical Pharmacology, vol. 35, No. 2, pp. 307–310, 1986.

Leach et al, "Pharmacological Studies on Lamotrigine, A Novel Potential Antiepileptic Drug: II. Neurochemical Studies on the Mechanism of Action", Epilepsia, 27(5):490–497, 1986.

Miller et al, "New Anticonvulsant Drugs", John Libbey & Company Ltd., 1986, pp. 165–177.

Nichol et al, "Lipid–Soluble Diaminopyrimidine Inhibitors of Dihydrofolate Reductase", Cancer Treatment Reports, vol. 61, No. 4, Jul. 1977, pp. 559–564.

Serano et al, "Evaluation of the Lipid–Soluble Diaminopyrimidines, Metoprine and Etoprine, in the Avian Sarcoma Virus Rat Glioma Model", Cancer Treatment Reports, vol. 66, No. 1, Jan. 1982, pp. 99–106.

Sternberg et al, "Phase II Evaluation of Metoprine in Advanced Pancreatic Adenocarcinoma", Cancer Treatment Reports, vol. 68, No. 7–8, Jul./Aug. 1984, pp. 1053–1054.

Tuomisto et al, "Is Histamine An Anticonvulsive Inhibitory Transmitter?", Neuropharmacology, vol. 25, No. 8, pp. 955–958, 1986.

Tuomisto et al, "Inhibition of Sound–Induced Convulsions by Metoprine in the Audiogenic Seizure Susceptible Rat", Agents and Actions, vol. 20, 3/4 (1987), pp. 252–254.

Zawilska et al, "Changes in the Rat Brain Histamine Content Following Metoprine and Other Histamine–Methyltransferase (HMT) Inhibitors", Pol. J. Pharmacol, Pharm., 1985, 37, pp. 821–830.

Primary Examiner—Bernard Dentz

[57] ABSTRACT

A class of substituted phenylpyrimidine compounds are disclosed which are potent inhibitors of the excitatory amino acid, glutamate. Such compounds are useful in the treatment or prevention of a range of CNS disorders including cerebral ischaemic damage and epilepsy.

12 Claims, No Drawings

TREATMENT OF DAMAGE FROM A STROKE USING 4-AMINO(4-METHYLPIPERAZIN-1-YL)-5-(2,3,5-TRICHLOROPHENYL)PYRIMIDINE

This is a Division of application Ser. No. 07/444,963, filed Dec. 4, 1989 now abandoned.

The present invention relates to a class of pyrimidine compounds which are useful in the treatment of central nervous system (CNS) diseases and disorders such as the prevention of cerebral ischaemic damage, to pharmaceutical compositions containing them, to their use in the treatment of such disorders, and to methods of preparing them.

Glutamate is an excitatory amino acid which functions as a neurotransmitter. However, when its extracellular concentration is sufficiently high, glutamate acts as a powerful neurotoxin, capable of killing neurones in the central nervous system, (Rothman & Olney (1986) Prog. Brain. Res., 63, 69). The neurotoxic effect of glutamate has been implicated in a number of central nervous system disorders and disease states including cerebral ischaemic damage, epilepsy and chronic neurodegenerative disorders, such as Alzheimer's disease, motor system disorders, and Huntington's chorea, (*Meldrum* Clinical Science (1985) 68 113–122). In addition, glutamate has been implicated in other neurological disorders such as manic depression, depression, schizophrenia, high pressure neurological syndrome, chronic pain, trigeminal neuralgia and migraine.

In European Patent application No. 21121 there is disclosed a group of 3,5-diamino-6-(substituted phenyl)-1,2,4-triazines which are active in the treatment of CNS disorders, for example in the treatment of epilepsy. One compound described in that application, 3,5-diamino-6-(2,3-dichlorophenyl)-1,2,4-triazine (lamotrigine), has been shown to inhibit the release of the excitatory amino acids, glutamate and aspartate, (Leach et al Epilepsia 27, 490–497 1986, A. A. Miller et al New anticonvulsant drugs. Ed. Meldrum and Porter 165–177, 1987).

The present inventors have now found that a series of substituted pyrimidine compounds, as defined in Formula I, are potent inhibitors of glutamate release; these compounds are useful in the treatment of the above mentioned disorders and disease states of the central nervous system. The pyrimidine compounds of formula I are also inhibitors of aspartate release.

Thus in a first aspect of the present invention there is provided the use of a compound of Formula I or an acid addition salt thereof in the manufacture of a medicament for treating or preventing CNS disorders or diseases of a mammal, wherein

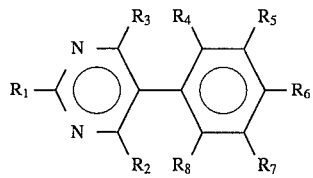

in Formula I, $R_1$ and $R_2$ are the same or different and are selected from hydrogen, halo, hydroxy, alkoxy, alkyl, alkylthio and a group $NR^1R^{11}$ where $R^1$ and $R^{11}$ are the same or different and are selected from hydrogen, alkyl, aryl and arylalkyl or together with the nitrogen atom to which they are attached form a cyclic ring optionally substituted with one or more alkyl groups and optionally containing a further heteroatom;

$R_3$ is hydrogen, alkyl optionally substituted by one or more halo radicals, or is amino, alkylamino, dialkylamino, cyano, nitro, halo, carbamoyl, hydroxy, carboxy, alkoxy, alkylthio, alkylthioalkyl, $S(O)_n$alkyl, di(alkyloxy)alkyl, —C(R):NOH or —COR or —$CO_2R$ wherein R is hydrogen or alkyl, or a group $CH_2X$ where X is hydroxy, alkoxy, aryloxy, arylalkyloxy, halo, cyano, —$NR^1R^{11}$ wherein $R^1$ and $R^{11}$ are as defined above, $S(O)_n$-alkyl where n is 1 or 2, or $SO_2NR^1R^{11}$;

each of $R_4$ to $R_8$ are the same or different and each is selected from hydrogen, halo, alkyl, perhaloalkyl, cyano, carbamoyl, carboxy, COR, nitro, amino, alkylsulphonylamino, alkoxy, $S(O)_n$-alkyl where n is 1 or 2, or $SO_2NR^1R^{11}$; or $R_4$ and $R_5$ or $R_5$ and $R_6$ together are the group —CH=CH—CH=CH— or the group —$CH_2$—$CH_2$—$CH_2$—$CH_2$— in which case both $R_7$ and $R_8$ are hydrogen; and optionally one of the nitrogen atoms in the pyrimidine ring may be N alkylated or optionally may be an N oxide;

the foregoing alkyl groups or moieties of alkyl-containing groups having from 1 to 6 carbon atoms, and the aryl groups or aryl moieties of aryl-containing groups having 6 or 10 carbon atoms.

Certain compounds of Formula I are chiral, and it will be appreciated that in these instances, Formula I encompasses both the racemic mixture and the individual enantiomers of such compounds. It will also be appreciated that when one or more of $R_1$, $R_2$ and $R_3$ are hydroxy, they may also exist in their tautomeric form.

A preferred class of compounds of Formula I which are potent inhibitors of glutamate are those wherein one of $R_1$ and $R_2$ is amino and the other is selected from amino, hydroxy, halo, morpholino, piperazinyl, N-alkylpiperazinyl, N,N-dialkylamino, N-alkylamino or alkylthio;

$R_3$ is alkyl optionally substituted by one or more halo radicals, or is alkyl, alkylthio, hydrogen, hydroxy, alkoxy, halo, carboxy, carbamoyl, or a group $CH_2X$ where X is hydroxy, phenoxy, benzyloxy, alkoxy or alkylthio;

one of $R_4$ and $R_5$ is halo and the other is selected from halo or hydrogen;

$R_6$ is halo, hydrogen, nitro or amino;

$R_7$ is hydrogen, halo, cyano, alkylthio, $SO_2NR^1R^{11}$ alkyl, nitro, amino or methanesulphonamido; and $R_8$ is hydrogen or halo.

In the present invention, $R_1$ is preferably hydroxy, amino, N-alkylamino, N,N-dialkylamino, morpholino, piperazinyl, N-alkylpiperazinyl;

$R_2$ is preferably chloro, amino, N,N-dialkylamino or piperiding;

$R_3$ is preferably hydrogen, alkyl, methoxymethyl, trifluoromethyl, benzyloxymethyl, phenoxymethyl or methylthiomethyl;

$R_4$ to $R_8$ are preferably selected from hydrogen and chloro. Preferably the alkyl moieties contain from 1 to 4 carbon atoms.

In Formula I, advantageously at least one of $R_1$ and $R_2$ is amino and the other is amino, piperazinyl or N-methylpiperazinyl, N-alkylamino, N,N-dialkylamino; and $R_3$ is hydrogen, methyl, trifluoromethyl or methoxymethyl.

It is a preferred feature of Formula I that two of $R_4$, $R_5$ and $R_7$ are chloro, in particular it is preferred that all of $R_4$, $R_5$ and $R_7$ are chloro. Such compounds are highly potent inhibitors of glutamate release. Preferred examples of the group $NR^1R^{11}$ are amino, N-methylamino, N-ethylamino, N,N-dimethylamino, piperazinyl, N-methylpiperazinyl, piperidinyl, and morpholino.

An especially preferred class of compounds within Formula I are those wherein $R_1$ is selected from amino, piperazinyl, N-methylpiperazinyl. N-morpholino, N,N-dimethylamlno, and N-ethylamino;

$R_2$ is amino;

$R_3$ is selected from trifluoromethyl, hydrogen, methyl, benzyloxymethyl, methoxymethyl and methylthiomethyl;

$R_4$ is chloro; and at least one of $R_5$, $R_6$ and $R_7$ is chloro, and the remainder are selected from hydrogen, chloro and nitro; and $R_8$ is hydrogen or $R_4$ and $R_8$ are both hydrogen, $R_5$ and $R_7$ are both chloro and $R_6$ is selected from hydrogen chloro and nitro.

The present invention also provides a subclass of compounds of Formula I, which whilst being potent inhibitors of glutamate release show only weak (ie. having an $IC_{50}$ of >20 μm) or insignificant inhibitory effects on the enzyme dihydrofolate reductase. Accordingly, in a preferred embodiment of the present invention there is provided compounds of Formula I where $R_1$ to $R_8$ are hereinbefore defined with the proviso that when $R_7$ is halo, then $R_3$ is hydrogen, perhaloalkyl, methyl or methoxymethyl and/or $R_6$ is nitro and/or $R_1$ is N-alkylpiperazinyl, morpholino, N,N-dimethylamino, piperazinyl or N-ethylamino; or with the proviso that when $R_6$ is chloro then $R_4$ is halo, and $R_3$ is hydrogen, perhaloalkyl, methoxymethyl. methyl or halo and/or $R_1$ is N-methylpiperazinyl, piperazinyl, morpholino or N,N-(methylamino, or N-ethylamino.

Compounds of Formula I may be used in the treatment or prophylaxis of acute and chronic disorders of the mammalian central nervous system. The acute condition comprises cerebral ischaemia which may arise from a variety of causes including stroke, cardiac arrest, bypass surgery, neonatal anoxia and hypoglycaemia; and also physical injury or trauma of the spinal cord or brain. Chronic neuro- degenerative disorders which may be treated include Alzeheimer's disease, Huntington's chorea, Olivopontocerebellar atrophy, motor system disorders. Other neurological conditions which may be treated with a compound of Formula I include depression, manic depression, schizophrenia, chronic pain, epilepsy, trigeminal neuralgia and migraine.

In a further aspect, the present invention provides a method of treatment or prevention of a CNS disorder or disease of a mammal, including man, comprising the administration to the mammal of a non-toxic effective amount of a compound of Formula I or an acid addition salt thereof.

In particular, the present invention provides a method of treating a mammal predisposed to or having neurotoxic extracellular glutamate levels of the central nervous system comprising the administration to the mammal of a non-toxic effective amount of a compound of Formula I or an acid addition salt thereof.

Certain substituted phenylpyrimidines of the present invention are known in the art as having antimalarial activity. See for example Brit. J. Pharmacol. 6, 185–200 (1951); JACS, 73, 3763-70, (1951). Other phenylpyrimidines are known from Chem. Biol. Pteridineso 463–468, (1982) and Pharmacotherap.Budesinsky, p.129–141, (1963), ed. Oldrich Hanc.

Nonetheless, certain compounds of the present invention are novel and accordingly the present invention provides a compound of Formula I or an acid addition salt thereof wherein $R_1$ to $R_8$ are as hereindefined, with the proviso that at least one of $R_4$ to $R_8$ is other than hydrogen, and further with the proviso that when $R_1$ and $R_2$ are both amino, or when $R_1$ is hydroxy and $R_2$ is amino, and $R_3$ is alkyl or hydrogen, and $R_7$ is hydrogen, then $R_4$ and $R_5$ are both halo.

Other novel compounds of the present invention are those where $R_1$ to $R_3$ and $R_8$ are as hereinbefore defined and one of $R_4$ or $R_5$ is other than hydrogen, and $R_7$ is halo, alkyl, perhaloalkyl, cyano, nitro, amino, alkylthio, S(O)n-alkyl or $S(O)_2NR^1R^{11}$.

A third class of novel compounds of the present invention are those of Formula I where $R_1$ is morpholino, piperazinyl, N-alkylpiperazinyl, N,N-dialkylamino, N-alkylamino or alkylthio and $R_2$ to $R_8$ are as hereinbefore defined.

A fourth class of novel compounds of the present invention are those of Formula I where $R_1$ and $R_2$ are as hereinbefore defined; and $R_3$ is alkoxy, alkylthio or alkyl substituted by one or more halo radicals, or is a group $CH_2X$ where X is alkylthio, aryloxy, arylalkyloxy, alkyloxy or hydroxy; $R_4$ to $R_6$ are the same or different and are each selected from hydrogen, halo, perhaloalkyl, cyano, nitro, amino or alkylthio; $R_7$ is halo, alkyl, perhaloalkyl, cyano, nitro, amino, or a group $SO_2N(R^{111})_2$ wherein $R^{111}$ is alkyl; and $R_8$ is hydrogen or halo.

A fifth class of novel compounds of the present invention are those of Formula I where $R_1$ and $R_2$ and $R_4$ to $R_8$ are as hereindefined, and $R_3$ is alkoxy, aryloxy, arylalkyloxy or alkylthio. Preferred novel compounds of the present invention include the following, the numbers referring to the Examples hereinafter appearing:

EXAMPLE NO.

1. 4-Amino-2-(4-methylpiperazin-1-yl)-5-(2,3,5-trichlorophenyl-6-trifluoromethylpyrimidine 2. 2,4-Diamino-5-(2,3,5-trichlorophenyl)-6-methoxymethylpyrimidine 3. 4-Amino-2-(4-methylpiperazin-1-yl)-5-(2,3,5-trichlorophenyl) pyrimidine 4. 2,4-Diamino-5-(2,3,5-trichlorophenyl)-6-trifluoromethylpyrimidine 5. 2,4-Diamino-5-(4-nitro-2,3,5-trichlorophenyl)pyrimidine 6. 2,4-Diamino-5-(2,3,5-trichlorophenyl)-6-methylpyrimidine 7. 4-Amino-2-N-morpholino-5-(2,3,5-trichlorophenyl)-6-trifluoromethylpyrimidine 8. 4-Amino-2-N,N-dimethylamino-5-(2,3,5-trichlorophenyl)-6-trifluoromethylpyrimidine 9. 4-Amino-2-morpholino-N-5-(2,3,5-trichlorophenyl)pyrimidine 10. 4-Amino-2-N,N-dimethylamino-5-(2,3,5-trichlorophenyl)pyrimidine 11. 4-Amino-6-methyl-2-(4-methylpiperazin-1-yl)-5-(2,3,5-trichlorophenyl)pyrimidine 14. 2,4-Diamino-5-(2,3-dichlorophenyl)-6-trifluoromethylpyrimidine 15. 2,4-Diamino-5-(2,3-dichlorophenyl)-6-methylpyrimidine 16. 2,4-Diamino-5-(2,3-dichlorophenyl)-6-methoxymethylpyrimidine 25. 204-Diamino-5-(2,4-dichlorophenyl)-6-trifluoromethylpyrimidine 26. 6-Benzyloxymethyl-2,4-diamino-5-(2,4-dichlorophenyl)pyrimidine 27. 2-N-methylpiperazinyl-4-amino-5-(2,4-dichlorophenyl)pyrimidine 28. 2,4-Diamino-5-(2,5-dichlorophenyl)-6-trifluoromethylpyrimidine 29. 2,4-Diamino-5-(2,3,5-trichlorophenyl)pyrimidine 36. 4-Amino-5-(3,5-dichlorophenyl)-6-methyl-2-(4-methylpiperazin-1-yl)pyrimidine 58. 4-Amino-2-N-ethylamino-5-(2,3,5-trichlorophenyl)pyrimidine 79. 4-Amino-2-N-methylamino-5-(2,3,5-trichlorophenyl)pyrimidine or an acid addition salt thereof.

Suitable acid addition salts of the compounds of Formula I include those formed with both organic or inorganic acids. Such acid addition salts will normally be pharmaceutically acceptable. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. These salts can be made by reacting the compound as the free base with the appropriate acid.

While it is possible for the compounds of Formula I to be administered as the raw chemical, it is preferable to present them as a pharmaceutical formulation. The formulations of the present invention comprise a novel compound of Formula I, as above defined, or a pharmaceutically acceptable salt thereof together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral, parenteral (including subcutaneous, intradermal, intramuscular and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association a compound of Formula I or a pharmaceutically acceptable acid addition salt thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, an hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Tablets or other forms of presentation provided in discrete units may conveniently contain an amount of compound of the Formula I which is effective at such dosage or as a multiple of the same, for instance, units containing 5 mg to 500 mg, usually around 10 mg to 250 mg.

The compounds of the Formula I are preferably used to treat CNS disorders or diseases by oral administration or injection (intraparenteral or subcutaneous). The precise amount of compound administered to a patient will be the responsibility of the attendant physician. However the dose employed will depend on a number of factors, including the age and sex of the patient, the precise disorder being treated, and its severity. Thus for example when treating a patient with epilepsy the dose range is likely to be significantly lower than when treating a patient after stroke to alleviate cerebral ischaemic damage. Also the route of administration is likely to vary depending on the condition and its severity.

The compounds of the Formula I may be administered orally or via injection at a dose of from 0.1 to 30 mg/kg of mammal, e.g., human bodyweight per day more preferably 2 to 15 mg/kg of mammal, e.g., human bodyweight for each of the indications (disorders or diseases) previously indicated above, e.g., epilepsy and cerebral ischaemic damage after stroke. The dose range for adult humans is generally from 8 to 2,400 mg/day and preferably 35 to 1,050 mg/day. As certain compounds of the Formula I are long acting, it may be advantageous to administer an initial dose of 70 to 2,400 mg the first day then a lower dose of 20 to 1,200 mg on subsequent days. If the salt of the compound is administered in place of the compound, then the amount of salt administered is calculated in terms of the base.

Examples of such long acting compounds are:

2,4-diamino-5-(2,3,5-trichlorophenyl)-6-trifluoromethylpyrimidine; 4-amino-2-(4-methylpiperazin-1-yl) -5-(2,3,5-trichlorophenyl)-6-trifluoromethylpyrimidine; and 4-amino-2-(4-methylpiperazin-1-yl)-5-(2,3,5-trichlorophenyl) pyrimidine.

Long acting compounds in the clinic are advantageous because they are easier to manage. In the chronic situation, they may be administered without infusion and there is the minimum of direct medical intervention; also in acute conditions, patient compliance is encourage by minimising daily dosing. Conversely, short acting compounds such as:

2,4-diamino-5-(2,3,5-trichlorophenyl)-6-methoxymethylpyrimidine permit the clinician to control the pharmacological effect of the compound with great precision, since such compounds will be cleared from the central nervous system rapidly.

Compounds of the present invention may be made in any manner known to make analogous compounds known in the art (eg. JACS vol 73 (1951) 3763-70).

The present invention also provides a process for the preparation of a compound of Formula I or an acid addition salt thereof, which comprises the reaction of a compound of Formula II

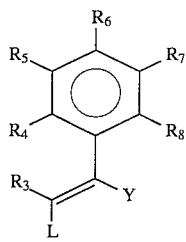

wherein $R_3$ to $R_8$ are as hereinbefore defined. L is a leaving group, and Y is cyano or carboxy, carbonyl, or alkoxycarbonyl with a compound or salt thereof of formula III

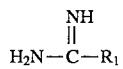

wherein $R_1$ is as hereindefined, and isolating the compound of Formula I as the free base or an acid addition salt thereof, and optionally converting the base into an acid addition salt thereof or into another acid addition salt, or into another compound of Formula I or an acid addition salt thereof.

It will be appreciated that certain compounds of Formula III for example where $R_1$ is hydroxy exists in the corresponding tautomeric form (eg. as urea).

As examples of interconversion of compounds of Formula I, when in the product of the above process one of $R_1$, $R_2$ or $R_3$ is hydroxy the compound may be halogenated for example using the Viismeier Haack reagent or phosphorus oxychloride ($POCl_3$), to the corresponding halo compound. This compound may be further converted into a compound of Formula I wherein $R_1$, $R_2$ or $R_3$ is alkylthio by reaction with the appropriate alkylthiolate or to the corresponding amino compound ($R_1$, $R_2$ or $R_3$ being $NR^1R^{11}$) by reaction with the appropriate amino compound in a suitable solvent such as an alkanol, eg. ethanol, or converted to a compound where $R_1$, $R_2$ or $R_3$ is alkoxy by reaction with appropriate alkoxide.

If it is required to make a compound of Formula I in which one of $R_4$ to $R_8$ is nitro, this can be made from the corresponding compound of Formula I where one of $R_4$ to $R_8$ is hydrogen by utilising standard nitration conditions, eg. sulphuric acid and potassium nitrate, and then further converted by standard reduction means to the corresponding amino compound, eg. utilising $PtO_2$, AcOH, $H_2$.

It will be appreciated that amino or halo compounds can be further converted to $R_4$ to $R_8$ as herewithin defined by standard interconversion, for example, via the diazonium salts. When $R_3$ is alkyl this may be converted into perhaloalkyl, or a halogenated alkyl moiety by reaction with the appropriate halogen or N-halo succinimide (NXS) in a suitable solvent such as acetic acid.

Compounds in which $R_3$ is $CH(OEt)_2$ may be converted into the corresponding aldehyde by hydrolysis with dilute acid(s) and thereafter reduced to the corresponding alcohol with a standard reducing agent (eg. sodium borahydride $NaBH_4$), or converted to the corresponding oxime (hydroxylamine hydrochloride in ethanol), which in turn can be converted to the corresponding cyano compound utilising, for example trifluoroacetic anhydride (TFAA), and then to the corresponding amido compound utilising concentrated sulphuric acid. Alternatively, the aldehyde may be oxidised with $KMnO_4$ (potassium permanganate) to give the corresponding acid, which may in turn be reacted with an alcohol to give the corresponding ester.

Where in the product of the above process $R_3$ is a group $CH_2OR$ where R is alkyl or arylalkyl this product may be converted to $CH_2X$ by reaction with HX (X=halo) in, for example acetic acid, and this further converted to the corresponding cyano compound, for example by treatment with sodium cyanide and DMF, or to fluoromethyl by treatment with for example cesium fluoride (CsF) or to a group $CH_2NR^1R^{11}$ by reaction with the appropriate amine. Alternatively, the group $CH_2OR$ can be dealkylated to give the corresponding alcohol, for example with $Me_3SiI$, and this further converted to fluoromethyl with diethylaminosulphur trifluoride (DAST).

Where $R_3$ to $R_8$ contains an alkylthio moiety, this can be oxidised to the corresponding sulphoxide and sulphone using for example MCPBA (metachloroperbenzoic acid).

It will be appreciated that other interconversions may be effected as required by those skilled in the art using standard methodologies. Examples of suitable leaving groups (L) include $C_{1-4}$ alkoxy, halo, $NR^1R^{11}$ as hereindefined eg. anilino, morpholino, $C_{1-4}$ alkylamino, benzylamino, or alkylthio. Preferably in Formula III, $R_1$ is hydroxy, alkoxy, alkylthio, or a group $NR^1R^{11}$ as herein defined. Advantageously $R_1$ is amino, alkylamino, dialkylamino. piperazinyl or N-methylpiperazinyl.

Preferably the reaction of the compound of Formula I and II is carried out in a non-aqueous solvent, for example an alkanol, eg. ethanol at elevated temperatures (eg. between 50° to 110° C.) in a base, preferably an alkanoxide, preferably under reflux using sodium ethoxide as the base.

Alternatively a compound of Formula I or an acid addition salt thereof may also be made by the reaction of a compound of Formula III with a compound of Formula IV

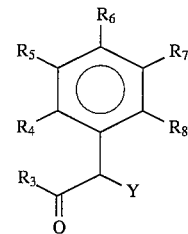

wherein $R_3$ to $R_8$ and Y are as herein defined. The reaction preferably takes place in a non-aqueous solvent, eg. alkanols, such as ethanol, and at elevated temperatures, preferably under reflux.

Compounds of formula IV can be made by methods known in the art (JACS, 1951, 73, 3763–3770).

Compounds of Formula II may be made by methods known in the art (JACS supra) for example by the reaction of a compound of Formula IV with diazomethane or with alkylorthoesters (JACS, 1952, 74, 1310–1313), or by condensation with an amine.

In Formula III when $R^1$ is piperazinyl or alkyl piperazinyl these can be made by standard methods for example by reaction of a known compound of Formula III where $R^1$ is alkylthio with the appropriate amine, eg. N-methylpiperazine. This reaction preferably takes place at room temperature in water.

Compounds of formula I may also be made by the reaction of a compound of Formula V

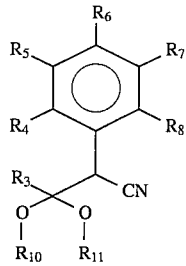

wherein Y and $R_3$ are as hereinbefore defined and $R_{10}$ and $R_{11}$ are alkyl or collectively form a group $(CR_2)_n$ where n is 2 to 4 and R is H or alkyl, with a compound of Formula III. Most preferably $R_1$ is amino, piperazinyl or methyl piperazinyl. Preferably the reaction is carried out in a non-aqueous solvent, eg. ethanol, under reflux using sodium ethoxide as the base.

Compounds of Formula I may also be prepared from the corresponding dihydropyrimidine by utilising standard dehydrogenation conditions, (eg. JCS, 1956, 1019).

Such dihydropyrimidine can be prepared by the reaction of a compound of Formula II where $R_3$ to $R_8$ are as defined and L is hydrogen with a compound of Formula III.

In the Examples of the invention set forth below, the chemical and other abbreviations used are standard in the art and have these meanings:

$NaBH_4$: sodium borohydride
$CHCl_3$: chloroform
$NaHCO_3$: sodium bicarbonate
$MgSO_4$: magnesium sulphate
$PBr_3$: phosphorus tribromide
DMF: dimethylformamide
KCN: potassium cyanide
$Et_2O$: diethyl ether
NaOEt: sodium ethoxide
EtOH: ethanol
$H_2SO_4$: sulphuric acid
AcOH: acetic acid
MeOH: methanol
$N_2$: nitrogen
HCl: hydrochloric acid
NaOH: sodium hydroxide
$SiO_2$: silica
DMSO: dimethylsulphoxide
Na: sodium
DME: dimethoxyethane
MeI: methyl iodide (iodomethane)
EtOAc: ethyl acetate
$CH_2Cl_2$: dichloromethane
$Et_3N$: triethylamine
$MeNH_2$: methylamine
$NH_4OH$: ammonium hydroxide
$SOCl_2$: thionyl chloride
THF: tetrahydrofuran
NaH: sodium hydride
$CCl_4$: carbon tetrachloride
DHFR: dihydrofolate reductase
$PtO_2$: platinum oxide (Adams' catalyst)
NXS: N-halo succinimide
$X_2$: halogen
TFAA: trifluoroacetic anhydride CsF: cesium fluoride
$Me_3SiI$: trimethylsilyliodide
DAST: diethylaminosulphur trifluoride
MCPBA: metachloroperbenzoic acid
AIBN: α,α'-azoisobutyronitrile 2,2'-azobis(2-methylpropionitrile)

EXAMPLE 1

Preparation of 4-Amino-2-(4-methylpiperazin-1-yl)-5-(2,3,5-trichlorophenyl-6-trifluoromethylpyrimidine 1. Preparation of N-methylpiperazinoformamidine hydriodide Thiourea (10.8 g) was dissolved in acetone (250 ml) at 50° C. Iodomethane (10 ml) was added and the reaction was stirred at 50° C. for 4 hours. After cooling, the solution was diluted with ether (1 liter) and the methiodide salt was filtered, washed with ether and dried in vacuo, 29.2 g, 113°–115° C. The methiodide salt (5 g) was dissolved in water, (30 ml) and N-methylpiperazine was added. The solution was stirred, with nitrogen bubbled through, at room temperature for 24 hours. The solution was concentrated vacuo. The residue was slurried with ethanol, filtered and dried in vacuo, 4.98 g, m.pt. 230°–242° C.

2. Preparation of 2,3,5-trichlorobenzylalcohol

To a solution of 2,3,5-trichlorobenzaldehyde (Aldrich, 50 gms) in ethanol (1.0L) at room temperature was added $NaBH_4$ (7.00 gms) and the resulting mixture stirred for 3.5 hours. The reaction was quenched with water, and the solvent evaporated in vacuo before partitioning the residue between $CHCl_3$ and saturated $NaHCO_3$ solution. The organic phase was washed with brine, dried over $MgSO_4$, filtered and the solvent evaporated in vacuo to leave a white solid. 43.00 gms, mp. 90°–93° C.

3. Preparation of 2,3,5-trichlorobenzyl bromide

To a solution of the alcohol in benzene (400 ml) under $N_2$ was added $PBr_3$ (126.58 gms), and the mixture stirred at 55°–60° C. for 3.5 hours. After cooling, the mixture was poured onto crushed ice (2L) and the benzene layer separated. The aqueous phase was washed with benzene (×3) and the combined benzene extracts washed with saturated $NaHCO_3$ solution and water, dried over $MgSO_4$, filtered and the solvent evaporated to leave a brownish liquid which solidified on standing, 37.53 gms, mp. 40°–42° C.

4. Preparation of 2,3,5-trichlorophenylacetonitrile

The bromide was suspended in DMF (130 ml)/water(86.67 ml) at 0° C. and KCN(12.99 gms) added in portions. After stirring at 30°–35° for 3 hours, the suspension was diluted with water and extracted with $Et_2O$. The combined ether extracts were washed with water, dried over $MgSO_4$, filtered and the solvent evaporated in vacuo. Chromatography on silica gel eluting with hexane to 20% ether-hexane gave the desired product as a white solid, 18.52 gms, mp. 60°–62° C.

5. Preparation of 2-(2,3,5-trichlorophenyl)-4,4,4-trifluoro-3-oxo-butyronitrile

To a solution of NaOEt (from 1.04 gms Na) in EtOH (60 ml) at room temperature under $N_2$ was added the nitrile (8.40 gms) followed by ethyl trifluoroacetate (6.57 gms) and the mixture stirred at reflux for 5 hours. After cooling, the solvent was removed in vacuo and the residue dissolved in water. The aqueous phase was washed with $Et_2O$ (discarded), acidified with $H_2SO_4$ and extracted with $Et_2O$. The combined $Et_2O$ extracts were washed with water, dried over MgSO$_4$, filtered and the solvent evaporated in vacuo to leave an oil. This was triturated with petroleum ether, and the solid filtered off and dried. The solid was azeotroped with toluene (×5), 4.89 gms, mp. 160°–163° C.

6. Preparation of 2-(2,3,5-trichlorophenyl)-4,4,4-trifluoro-3-methoxybut-2-enonitrile To a solution of the trifluoromethyl ketone in Et$_2$O (39.62 ml) at room temperature was added diazomethane (from 8.55 gms Diazald) in Et$_2$O (79.62 ml), and the resulting mixture left to stand at room temperature overnight. Excess diazomethane was then removed in vacuo into AcOH, and the residue was dissolved in Et$_2$O, dried over MgSO$_4$, filtered and the solvent evaporated in vacuo to leave a brownish oil, 5.20 gms.

7. Preparation of 4-Amino-2-(4-methylpiperazin-1-yl)-5-(2,3,5-trichlorophenyl)-6-trifluoromethylpyrimidine To a solution of NaOEt (from 0.144 g of Na) in EtOH (12.5 ml) was added N-methylpiperazinoformamidine hydriodide (1.39 g). After stirring for 10 minutes at room temperature a solution of the above intermediate (0.85 g) in EtOH (2.5 ml) was added and the resulting mixture was stirred at reflux for 4.5 hours. After cooling, the suspension was filtered, and the filtrate was evaporated to dryness in vacuo. Chromatography on silica gel, eluting with CHCl$_3$ –4% MeOH/CHCl$_3$, gave the desired product which was triturated with petroleum ether (b.p. 40°–60° C.) and dried in vacuo. 0.56 g, m.pt 127°–129° C.

8. 4-Amino-2-(4-methylpiperazin-1-yl)-5-(2,3,5-trichlorophenyl)-6-trifluoromethylpyrimidine methanesulphonate The phenyl pyrimidine base (9.6 g) was dissolved in absolute ethanol, cooled at 0° C., and methanesulphonic acid (2.14 g, 1.62 ml) was added. After stirring at room temperature for 2 hours, the solution was evaporated to dryness and the residue triturated with Et$_2$O, filtered and dried in vacuo to leave a beige coloured solid. This was dissolved in water (500 mls) and freeze-dried to leave 10.7 g as a tan coloured solid. The methanesulphonate salt could be further purified by triturating with $^i$BuOH (30 ml), filtering, dissolving in water and again freeze drying to leave the title product as a off-white solid. 8.33 g mp. 145°–7° C.

EXAMPLE 2

Preparation of
2,4-Diamino-5-(2,3,5-trichlorophenyl)-
6-methoxymethylpyrimidine

A. 2-(2,3,5-trichlorophenyl)-4-methoxy-3-oxo-butyronitrile

To a stirred refluxing solution of sodium ethoxide (from 1.38 g sodium) in ethanol (25 ml) was added over 5 minutes a mixture of 2,3,5-trichlorophenylacetonitrile (11 g) and ethyl methoxyacetate (8.85 g) in dry DME (25 ml). After 4 hours the mixture was cooled on ice and acidified by dropwise addition of acetic acid (ca. 6 ml), diluted with ice-water (150 ml) and extracted with dichloromethane (2×100 ml). The dichloromethane extract was washed with water, dried over MgSO$_4$ and concentrated giving a yellow solid, which was triturated with a little ether and filtered. 8.6 g Homogeneous by TLC (19:1 CH$_2$Cl$_2$:MeOH).

B. Preparation of 2,4-Diamino-5-(2,3,5-trichlorophenyl)-6-methoxymethylpyrimidine A suspension of the crude acyl acetonitrile (8.5 g) in ether (100 ml), cooled on ice was treated with an excess of an alcohol free solution of diazomethane in ether (0.035M). After one hour TLC (19:1 CH$_2$Cl$_2$:MeOH) showed no starting material. The solution was concentrated to give a brown waxy solid, which was used without further purification.

To a solution of sodium ethoxide (from 0.769 sodium) in ethanol (30 ml) was added guanidine hydrochloride (2.9 g). After 15 minutes a solution of the crude enol ether in ethanol (25 ml) was added and the mixture refluxed with stirring for 4 hours, cooled and concentrated. The residue was shaken with 2M NaOH (150 ml) and the dark solid filtered off, washed with water, dried in air and recrystallised from ethanol (150 ml). 5 g M.pt. 214°–216° C. TLC (1:9 MeOH:CHCl$_3$) Rf 0.35.

C. 2,4-Diamino-5-(2,3,5-trichlorophenyl)-6-methoxymethylpyrimidine ethanesulphate To a stirred suspension of the phenylpyrimidine (2 g) in ethanol (75 ml) was added dropwise ethanesulphonic acid (0.67 g) in ethanol (10 ml). After ca 30 minutes the solution became cloudy. Stirring was continued for a further 1.5 hours and the solvent then concentrated to ca 20 mls. Ether was added, the solid filtered off and washed with Et$_2$O before drying in vacuo, 2.17 g, m.pt. 265°–268° C.

EXAMPLE 3

Synthesis of 4-Amino-2-(4-methylpiperazin-1-yl)-
5-(2,3,5-trichlorophenyl)pyrimidine mesylate 1. Preparation of 2-(2,3,5-trichlorophenyl)-3-oxo-propionitrile, Sodium Salt 1. To a solution of NaOEt (from 0.803 g of sodium) in ethanol (55 ml) cooled in ice, under nitrogen, was added 2,3,5-trichlorophenyl acetonitrile (see Example 1.4). Ethyl formate (5.1 ml) was added and the mixture was stirred at room temperature overnight. After stirring for a further 2.5 hours at 50° C., the mixture was cooled and filtered. The filtrate was evaporated, and the residue was triturated with diethyl ether, filtered and dried (6.82 g).

2. Preparation of 2-(2,3,5-trichlorophenyl)-3-methoxyacrylonitrile

The above solid was dissolved in DMF (36 ml) and methyl iodide (2 ml) was added. The reaction vessel was sealed before stirring the contents at 40° C. for 3 hours. The solvent was then evaporated. The residue was partitioned between water and ethyl acetate. The organic phase was washed with water, dried (MgSO$_4$) and the solvent evaporated to give the crude product as a red-brown oil that solidified on standing (5.04 g)

3. Preparation of 4-Amino-2-(4-methylpiperazin-1-yl)-5-(2,3,5-trichlorophenyl)pyrimidine To a solution of NaOEt (from 0.21 g of sodium) in ethanol (20 ml) was added N-methylpiperazinoformamidine hydriodide (2.06 g) (see Example 1.1). After stirring for a further 10 minutes, the compound of Example 3.2 (1 g) was added and the mixture was stirred at reflux for 4 hours. The mixture was left standing at room temperature overnight and then filtered. The filtrate was concentrated and the residue was purified by chromatography on SiO$_2$, eluting with CHCl$_3$ to 4% MeOH/CHCl$_3$ to give the title compound as the free base. 0.89 g, mp. 16°–164° C. The free base (0.805 g) was then dissolved in ethanol (35 ml) and cooled in an ice bath. Methanesulphonic acid (0.21 g) was added and the reaction was stirred at room temperature for 2 hours. The solvent was then evaporated and the residue was triturated with diethyl ether, filtered, dissolved in cold water and freeze dried to give the title salt as a pale green solid, 0.98 g, mp. 143°–146° C.

EXAMPLE 4

Synthesis of 2,4-Diamino-5-(2,3,5-trichlorophenyl)-6-trifluoromethylpyrimidine

To a solution of NaOEt (from 0.88 g of Na) in EtOH (82 ml) was added guanidine hydrochloride (2.98 g). The resulting white suspension was stirred at room-temperature for 10 minutes. A solution of the enol ether (Example 1.6) in ethanol (27 ml) was added and the resulting mixture stirred at reflux for 4.25 hours. After cooling, the suspension was filtered, and the filtrate evaporated to dryness in vacuo. Chromatography on silica gel eluting with CHCl$_3$ to 2% MeOH:CHCl$_3$ gave the desired product which was triturated with Et$_2$O and dried in vacuo, 1.78 gms, m.p. 226°–227° C.

EXAMPLE 5

Preparation of 2,4-Diamino-5-(4-nitro-2,3,5-trichlorophenyl)pyrimidine

The compound from Example 29 was dissolved in concentrated sulphuric acid (2.5 ml), potassium nitrate (25.8 mg) added and the solution stirred for 3 hours. The solution was then poured onto ice and basified with 10N NaOH. The product was extracted with ethyl acetate (×3), dried over MgSO$_4$, filtered and the solvent evaporated. Chromatography on silica gel eluting with ethyl acetate gave the desired product, 40.7 mg, mp. 293°–295° C.

EXAMPLE 6

Preparation of 2,4-Diamino-5-(2,3,5-trichlorophenyl)-6-methyl pyrimidine

1. Preparation of 2-(2,3,5-trichlorophenyl)-3-oxobutyronitrile

To a solution of NaOEt (from 0.68 g of sodium) in ethanol (20 ml) was added 2,3,5-trichlorophenylacetonitrile (5 g) and ethyl acetate (4.43 ml). The mixture was heated under reflux, under nitrogen for 2.5 hours. The mixture was left standing at room temperature overnight. The mixture was then concentrated and the residue was dissolved in water. The aqueous phase was washed with ether, acidified with concentrated H$_2$SO$_4$ and extracted with ether. The extracts were bulked, dried (MgSO$_4$) and evaporated, 2.59 g, mp. 134°–135° C.

2. Preparation of 2-(2,3,5-trichlorophenyl)-3-methoxybut-2-enonitrile

To a solution of the ketone in ether (100 ml) at room temperature was added diazomethane (from 5.43 g Diazald) in ether (50 ml) and the resulting mixture was left to stand at room temperature overnight. The ether was then distilled off to leave the desired product, 2.45 g.

3. Preparation of 2,4-Diamino-5-(2,3,5-trichlorophenyl)-6-methylpyrimidine

Guanidine hydrochloride (3.87 g) was added to a solution of sodium ethoxide (from 1.01 g of sodium) in ethanol (80 ml). The resulting white suspension was stirred at room temperature for 10 minutes and then added to a solution of the enol ether (Example 6.2) (5.60 g) in ethanol (20 ml). The resulting mixture was stirred at reflux for 8 hours under nitrogen. After cooling, the suspension was filtered, and the filtrate evaporated to dryness in vacuo. Chromatography on silica gel eluting with CHCl$_3$ to 2% MeOH-CHCl$_3$ gave the desired product which was triturated with ether and dried in vacuo. Yield 1.70 g, mp. 236°–238° C.

EXAMPLE 7

Preparation of 4-Amino-2-N-morpholino-5-(2,3,5-trichlorophenyl)-6-trifluoromethylpyrimidine To a solution of NaOEt (from 0.144 g of Na) in EtOH (12.5 ml) was added morpholinoformamidine hydrobromide (1.08 g) (Lancaster Synthesis). The resulting white suspension was stirred at room temperature for 10 minutes. A solution of the enol ether (0.85 g) (Example 1.6) in EtOH (2.5 ml) was added and the resulting mixture was stirred at reflux for 4.5 hours. After cooling, the suspension was filtered, and the filtrate was evaporated to dryness in vacuo. Chromatography on silica gel, eluting with CHCl$_3$, gave the desired product which was triturated with petroleum ether (b.p. 40°–60° C.) and dried in vacuo, 0.47 g, mp. 177°–181° C.

EXAMPLE 8

Preparation of 4-Amino-2(-N,N-dimethylamino)-5-(2,3,5-trichlorophenyl)-6-trifluoromethyl pyrimidine To a solution of NaOEt (from 0.144 g of Na) in EtOH (12.5 ml) was added 1,1-dimethylguanidine sulphate (1.4 g), (Aldrich). The resulting white suspension was stirred at room temperature for 10 minutes. A solution of 2-(2,3,5-trichlorophenyl)-4,4,4-trifluoro-3-methoxybut-2-enonitrile (see Example 1.6) (0.85 g) in EtOH (2.5 ml) was added and the resulting mixture was stirred at reflux for 4.5 hours. After cooling, the suspension was filtered, and the filtrate was evaporated to dryness in vacuo. Chromatography on silica gel, eluting with CHCl$_3$, gave the desired product, 0.61 g, mp. 124°–126° C.

EXAMPLE 9

Synthesis of 4-Amino-2-N-morpholino-5-(2,3,5-trichlorophenyl)pyrimidine

To a solution of NaOEt (from 0.21 g of sodium) in ethanol (20 ml) was added morpholinoformamidine hydrobromide (1.6 g). After stirring for 10 minutes the adduct of Example 3.2 (1 g) was added and the mixture was stirred at reflux for 4 hours. The mixture was left standing at room temperature overnight and then filtered. The filtrate was concentrated and the residue was purified by chromatography on SiO$_2$ gel, eluting with CHCl$_3$ to give the desired product, 0.73 g, mp. 168°–170° C.

EXAMPLE 10

Synthesis of 4-Amino-2-(N,N-dimethylamino)-5-(2,3,5-trichlorophenyl)pyrimidine

To a solution of NaOEt (from 0.21 g of sodium) in ethanol (20 ml) was added 1,1-dimethylguanidine sulphate (2.07 g). After stirring for 10 minutes the adduct of Example 3.2 (1 g) was added and the mixture was stirred at reflux for 4 hours. The mixture was left standing at room temperature overnight and then filtered. The filtrate was concentrated and the residue was purified by chromatography on SiO₂, eluting with CHCl₃ to give the desired product, 0.69 g, mp. 145°–147° C.

EXAMPLE 11

Synthesis of
4-Amino-6-methyl-2-(4-methylpiperazin-1-yl)-
5-(2,3,5-trichlorophenyl)pyrimidine To a solution of NaOEt (from 0.16 g of sodium) in ethanol (15 ml) was added N-methylpiperazinoformamidine hydriodide (1.6 g). After stirring for 10 minutes the enol ether of Example 6.2 (0.82 g) in ethanol (5 ml) was added and the mixture was stirred at reflux for 5 hours. The mixture was left standing at room temperature overnight and then filtered. The filtrate was concentrated and the residue was purified by chromatography on SiO₂ gel, eluting with CHCl₃ to 4% MeOH/CHCl₃ to give the desired product, 0.31 g, mp. 156°–159° C.

EXAMPLE 12

Synthesis of
2,4-diamino-6-methyl-5-(2,3,5-trichloro-
4-nitrophenyl)pyrimidine 2,4-Diamino-6-methyl-5-(2,3,5-trichlorophenyl)pyrimidine (0.152 g) (Example 6) was dissolved in concentrated sulphuric acid and potassium nitrate (50 mg) was added. The solution was stirred at room temperature overnight, then poured onto ice and basified with 0.880 ammonia. The product was extracted into ethyl acetate, bulked, dried (MgSO₄) and evaporated. The residue was purified by chromatography on SiO₂ gel, eluting with EtOAc to 8% MeOH/EtOAc to give the desired product, 0.13 g, mp. 313°–315° C.

EXAMPLE 13

Synthesis of
4-Amino-2-(N,N-dimethylamino)-6-methyl-
5-(2,3,5-trichlorophenyl)pyrimidine To a solution of NaOEt (from 0.16 g of sodium) in ethanol (15 ml) was added 1,1-dimethylguanidine sulphate (1.6 g). After stirring for 10 minutes the enol ether of Example 6.2 (0.82 g) in ethanol (5 ml) was added and the mixture was stirred at reflux for 5 hours. The mixture was left standing at room temperature overnight and then filtered. The filtrate was concentrated and the residue was purified by chromatography on SiO₂ gel, eluting with CHCl₃ to give the desired product, 54 mg, mp. 151°–153° C.

EXAMPLE 14

Synthesis of 2,4-Diamino-5-(2,3-dichlorophenyl)
-6-trifluoromethylpyrimidine

1. Preparation of 2,3-dichlorobenzyl alcohol

To a solution of 2,3-dichlorobenzaldehyde (Aldrich, 50 gms) in alcohol (800 mL) at room temperature was added NaBH₄ (8.54 gms) and the resulting mixture stirred for 1.5 hours. The reaction was quenched with water and the solvent evaporated in vacuo before partitioning the residue between CHCl₃ and saturated NaHCO₃ solution. The organic phase was washed with brine, dried over MgSO₄, filtered and the solvent evaporated in vacuo to leave a white solid, 48.38 gms, mp. 87°–87.5° C.

2. Preparation of 2.3-dichlorobenzyl Bromide

To a solution of the alcohol in benzene (500 ml) under N₂ was added PBr₃ (167.8 gms), and the mixture stirred at 55°–60° C. for 3.5 hours. After cooling, the mixture was poured onto crushed ice (2L) and the benzene layer separated. The aqueous phase was washed with benzene (×3) and the combined benzene extracts washed with saturated NaHCO₃ solution and water, dried over MgSO₄, filtered and the solvent evaporated to leave a brownish liquid which solidified on standing. 37.53 gms, mp. 31°–32° C.

3. Preparation of 2,3-dichlorophenylacetonitrile

The bromide was suspended in DMSO (155 ml)/water (105 ml) at 0° C. and KCN (20.24 gms) added in portions. After stirring at 30°–35° C. for 2 hours, the suspension was diluted with water and extracted with Et₂O. The combined ether extracts were washed with water, dried over MgSO₄, filtered and the solvent evaporated in vacuo to leave a white solid, 27.52 gms, mp. 64°–67° C.

4. Preparation of 2-(2,3-dichlorophenyl)-4,4,4-trifluoro-3-oxo-butyronitrile

To a solution of NaOEt (from 1.48 gms Na) in EtOH (25 ml) at room temperature under N₂ was added the nitrile (10.0 gms) followed by ethyl trifluoroacetate (9.3 gms) and the mixture stirred at reflux for 5 hours. After cooling, the solvent was removed in vacuo and the residue dissolved in water. The aqueous phase was washed with Et₂O (discarded), acidified with H₂SO₄ and extracted with Et₂O. The combined Et₂O extracts were washed with water, dried over MgSO₄, filtered and the solvent evaporated in vacuo to leave an oil. This was triturated with petroleum ether, and the solid filtered off and dried. 9.56 gms, mp. 74°–75° C.

5. Preparation of 2-(2,3-dichlorophenyl)-4,4,4-trifluoro-3-methoxybut-2-enonitrile To a solution of the trifluoromethyl ketone in Et₂O (90 ml) at room temperature was added diazomethane (from 19.35 gms Diazald) in Et₂O (180 ml), and the resulting mixture left to stand at room temperature overnight. Excess diazomethane was then removed in vacuo into AcOH, and the residue was dissolved in Et₂O, dried over MgSO₄, filtered and the solvent evaporated in vacuo to leave a brownish solid, 6.44 gms.

6. Preparation of 2,4-Diamino-5-(2,3-dichlorophenyl)-6-trifluoromethylpyrimidine To a solution of the above enol ether in ethanol (37 ml) was added guanidine hydrochloride (1.92 gms) followed by a solution of NaOEt (from 540 mgs of Na) in EtOH (90 ml), and the resulting mixture stirred at reflux for 3 hours. After cooling, the suspension was filtered, and the filtrate evaporated to dryness in vacuo. Chromatography on silica gel eluting with CHCl₃ to 2% MeOH-CHCl₃ gave the desired product which was triturated with Et₂O and dried in vacuo, 673 mg, m. pt.218°–9° C.

7. 2,4-Diamino-5-(2,3-dichlorophenyl)-6-trifluoromethylpyrimidine methanesulphonate To a suspension of the free base (100 mg) in ethanol was added methanesulphonic acid (30 mg) and the resulting clear solution stirred at room temperature for 2 hours. The solution was evaporated to dryness, and the resulting solid triturated with ether, filtered, and dried in vacuo, 107 mg, m.pt. 253°–256° C.

8. 2,4-Diamino-5-(2,3-dichlorophenyl)-6-trifluoromethylpyrimidine hydrochloride

To a solution of the free base (150 mg) in methanol was added ethereal hydrogen chloride. After stirring, the solvent was evaporated to dryness and the resulting solid triturated

EXAMPLE 15

Synthesis of 2,4-Diamino-5-(2,3-dichlorophenyl)-6-methylpyrimidine

This compound was made in an analogous manner to the compound of Example 6 from 203-dichlorophenylaceonitrile, m.pt. 245°–247° C.

EXAMPLE 16

Synthesis of 2,4-Diamino-5-(2,3-dichlorophenyl)-6-methoxymethylpyrimidine

1. Preparation of 2-(2.3-dichlorophenyl)-4-methoxy-3-oxo-butyronitrile

To a stirred refluxing solution of NaOEt (from 1.38 gms Na) in EtOH (25 ml) was added a mixture of ethyl methoxyacetate (8.85 gms) and 2,3-dichlorophenylacetonitrile (Example 14.3) (9.3 g) dissolved in DME (20 ml) during 5 minutes. After 5 hours a precipitate had appeared (sodium salt of product). The mixture was cooled and filtered, the filtrate evaporated to dryness in vacuo and the residue partitioned between ether and water (the ether phase was discarded). The aqueous residue was acidified with 2N $H_2SO_4$ and extracted with ether (2×). The combined $Et_2O$ extracts were washed with water, dried over $MgSO_4$, filtered and evaporated in vacuo to give a yellow solid (a). The sodium salt (above) was dissolved in water and the solution extracted with ether and discarded. The aqueous solution was acidified with 2N $H_2SO_4$ and extracted with ether. The ether extract was washed with water, dried over $MgSO_4$, filtered and evaporated in vacuo to give a white solid (b).

The above products (a) and (b) were combined to give a yield of 10.4 gms which was used without further purification. Single spot by TLC (19:1 $CH_2Cl_2$: MeOH) Rf 0.35.

2. Preparation of 2-(2,3-dichlorophenyl)-3,4-dimethoxy-but-2-enonitrile

To a stirred solution of the above nitrile (9.4 gms) in Ether was added in portions diazomethane (0.4–0.45M) in ether. Initially vigorous frothing occurred and after further addition no immediate reaction was produced. The mixture was left stirring at room temperature for 3 hours and evaporated in vacuo, into AcOH to give the enol ether.

3. Preparation of 2,4-Diamino-5-(2,3-dichlorophenyl)-6-methoxymethypyrimidine

To a solution of NaOEt (from 0.92 gms Na) in EtOH (40 ml) was added guanidine hydrochloride (3.44 gms). A solution of the enol ether (above) in EtOH (30 ml) was added and the mixture refluxed for Ca. 3 hours. After cooling, the solvent was evaporated off in vacuo and the residue treated with 5N NaOH (ca. 50 ml). The red solid was filtered off, dissolved in AcOH (ca. 20 ml), diluted with water (40 ml), treated with charcoal, and filtered. The filtrate (yellow solution) was made alkaline with 2N NaOH, and the white precipitate filtered off, dried and recrystallised from EtOH, 4.39 gms, mp. 237°–240° C.

EXAMPLE 17

Preparation of 2,4-Diamino-5-(1-naphthyl)pyrimidine

To a solution of NaOEt (from 1.45 gms Na) in ethanol (60 ml) at room temperature under $N_2$ was added 1-naphthylacetonitrile (Aldrich, 10.02 gms). After stirring for 10 minutes, ethyl formate (8.88 gms) was added and the mixture stirred at reflux for 5 hours. The mixture was cooled, the solvent evaporated, and the residue triturated with $Et_2O$ before filtering and drying the solid in vacuo (6.86 gms).

The above solid was dissolved in DMF (45 ml), methyliodide (5.4 gms) added, and the reaction vessel sealed before stirring the contents at 40° C. for 4 hours. The solvent was then removed in vacuo, and the residue partitioned between EtOAc and water. The organic phase was washed with water, dried over $MgSO_4$, filtered, and the solvent evaporated in vacuo to leave the crude product as a viscous reddish oil (5.4 gms).

To a solution of NaOEt (from 1.19 gms of Na) in ethanol (80 ml) was added guanidine hydrochloride (4.94 gms). After stirring for a further 5 minutes, the above intermediate in ethanol was added and the resulting mixture stirred at reflux for 3.5 hours. After cooling, the solvent was removed in vacuo and the residue partitioned between $CHCl_3$ and water. The organic phase was washed with water, dried over $MgSO_4$, filtered and the solvent evaporated to leave a pale yellow solid. Chromatography on $SiO_2$ eluting with $CHCl_3$ to 4% $CHCl_3$:MeOH, followed by recrystallisation from ethanol gave the desired product as a white solid. 2.82 gms, mp.171°–3° C.

EXAMPLE 18

Preparation of 2,4-Diamino-5-(2,3-dichlorophenyl)-6-fluoromethylpyrimidine 1. 1,2,4-Diamino-5-(2,3-dichlorophenyl)-6-(diethoxymethyl)pyrimidine To a stirred refluxing solution of NaOEt (from 1.38 g sodium) in ethanol (25 ml) was added over 5 minutes a mixture of ethyl diethoxyacetate (13.21 g; 75 mmol) and (Example 14.3) 2,3-dichlorophenylacetonitrile (9.3 g; 50 mmol) in dry dimethoxyethane (20 ml). After 4 hours cooled and evaporated in vacuo. The residue was partitioned between water (100 ml) and ether (100 ml), the ether phase discarded and the aqueous residue acidified with 1N $H_2SO_4$. Extraction with $CH_2Cl_2$ gave the acyl acetonitrile (13.47 g), which was used without further purification.

To a stirred solution of the above acyl acetonitrile in ether (100 ml), cooled on ice was added in portions a solution of diazomethane (ca. 3 g) in ether. After 2 hours the solution was evaporated in vacuo to give the desired enol ether as an oil, which was used without further purification.

To a solution of NaOEt (from 1.4 g sodium) in ethanol (50 ml) was added guanidine hydrochloride (4.8 g; 50 mmol). A solution of the above enol ether in ethanol (20 ml) was added and the mixture refluxed for 4 hours cooled, and concentrated in vacuo to ca. 30 ml and diluted with water to give a dark purple solid which was filtered, dissolved in $CH_2Cl_2$, washed with water, dried over $MgSO_4$ and evaporated in vacuo. The residue was triturated with ethanol (50 ml) and filtered to give the desired product (8.4 g) which was used without further purification. (mp. 214°–217° C.).

2. 2,4-Diamino-5-(2,3-dichlorophenyl)pyrimidine-6-carboxaldehyde

A mixture of the above acetal (7 g) and 0.4M HCl (150 ml) was refluxed with stirring for 1 hour, cooled on ice and neutralised with 2M NaOH. The mixture was filtered, washed with water and dried in air to give the desired product (6.2 g), which was used without further purification.

3. 2,4-Diamino-5-(2,3-dichlorophenyl)-6-hydroxymethylpyrimidine

To a stirred solution of the above aldehyde (2.8 g; 10 mmol) in a mixture of dimethoxyethane (15 ml) and ethanol (15 ml) was added in portions sodium borohydride (110 mg; 3 mmol). After 30 minutes the solution was treated with water (50 ml) and a few drops of acetic acid added to destroy excess borohydride. Extracted with dichloromethane (2×50 ml), washed with water and the extract was then dried over MgSO$_4$. Evaporation of the solvent in vacuo gave a pink solid, which was triturated with ether, filtered and dried (1.6 g). Recrystallisation from methanol (50 ml) gave the desired product as fine colourless crystals. 0.65 g, m.p. 173°–6° C.

4. 2,4-Diamino-5-(2,3-dichlorophenyl)-6-fluoromethylpyrimidine

To a stirred suspension of 2,4-diamino-5-(2,3-dichlorophenyl)-6-hydroxymethylpyrimidine (185 mg; mmol) in dry dichloromethane (25 ml), under nitrogen at −70° C., was added dropwise diethylaminosulphur trifluoride (263 μl; 2 mmol). The mixture was allowed to warm to 0° C. and kept at this temperature for 4 hours. After cooling to −70° C. the mixture was quenched with aqueous sodium bicarbonate, extracted with dichloromethane (2×50 ml), washed with saturated brine and dried (MgSO$_4$). Concentration gave a colourless gum (0.2 g). Chromatography on silica gel, eluting with 0.01:1.19 Et$_3$N:MeOH:CH$_2$Cl$_2$ gave the desired product which was triturated with CCl$_4$ and dried in vacuo. 111 mg, mp. 224°–6° C.

EXAMPLE 19

2,4-Diamino-5-(2,3-dichlorophenyl)-6-phenoxymethylpyrimidine

To a stirred solution of NaOEt (from 1.38 g sodium), in ethanol (70 ml) at reflux, was added over 10 minutes a mixture of 2,3-dichlorophenylacetonitrile (9.3 g) and ethyl phenoxyacetate (13.5 g) in dry dimethoxyethane (50 ml). After stirring at reflux for 3 hours the mixture was cooled, filtered and the solvents evaporated in vacuo. The residue was dissolved in water, washed with ether (discarded), acidified with 2N hydrochloric acid and extracted with dichloromethane. The combined extracts were washed with brine, dried (MgSO$_4$) and evaporated in vacuo leave a tan coloured solid (8 g), which was used without further purification.

To a suspension of the crude acyl acetonitrile (8 g) in ether (150 ml) was added in portions an excess of a solution of diazomethane in ether. After stirring for 1 hour at room temperature the solution was concentrated in vacuo to give the enol ether, which was used without further purification.

To a solution of sodium ethoxide (from 0.63 g sodium) in ethanol (25 ml) at room temperature was added guanidine hydrochloride (2.39 g). After 15 minutes a solution of the above enol ether in ethanol (25 ml) was added and the mixture stirred at reflux for 4 hours. After cooling the solvent was evaporated in vacuo. The residue was suspended in 2N NaOH (75 ml), filtered, washed with water, dried in air and recrystallised from ethanol to give the desired product as a colourless solid. 3.82 g, mp. 211°–213° C.

EXAMPLE 20

2,4-Diamino-5-(2,3-dichlorophenyl)-6-methylthiomethylpyrimidine

To a stirred solution of NaOEt (from 1.38 g sodium), in ethanol (25 ml) at reflux, was added over 5 minutes a mixture of 2,3-dichlorophenylacetonitrile (9.3 g) and ethyl methylthioacetate (10.07 g) in dry dimethoxyethane (20 ml). After stirring at reflux for 5 hours the mixture was cooled on ice, acidified with acetic acid (5 ml), poured into cold water and extracted with dichloromethane. The combined extracts were washed with water, dried (MgSO$_4$) and concentrated to give a yellow oil which was used without further purification.

The crude acyl acetonitrile was heated under N$_2$ with triethyl orthoformate (40 ml) at 140°–150° C. for 4 hours, distilling off low boiling material. After cooling, the mixture was concentrated in vacuo to leave a dark oil (15.2 g). The oil was dissolved in ethanol (20 ml) and added to a mixture of guanidine hydrochloride (4.8 g) and sodium ethoxide (from 1.38 g sodium) in ethanol (50 ml). After stirring at reflux for 4 hours the mixture was cooled and concentrated in vacuo. The residue was shaken with 5M NaOH to give a dark oil, which was extracted with dichloromethane, washed with water and dried (MgSO$_4$). Concentration in vacuo left a dark gum. The desired product crystallised from ethanol (20 ml) as a light tan solid, 0.57 g, mp. 205°–7° C.

EXAMPLE 21A

Preparation of 2,4-Diamino-5-(2,3-dichlorophenyl)pyrimidine a. 2-(2,3-dichlorophenyl)-3-oxo-propionitrile To a solution of NaOEt (from 3.63 gms Na) in ethanol (500 ml) was added 2,3-dichlorophenylacetonitrile (Example 14.3) in ethanol (150 ml). Ethyl formate (16.67 gms) was then added and the mixture stirred at 80° C. for 45 minutes, before adding a further quantity of ethyl formate (2.78 gms). After stirring at 80° C. for a further 1.5 hours, the precipitate was filtered off and dried in vacuo. The solid was dissolved in water, filtered, acidified with concentrated hydrochloric acid and the precipitate filtered off and dried in vacuo, 14.35 gms, 45% yield.

b. A solution of the above product, ethylene glycol (9.19 gms) and p-toluene-sulphonic acid (8.9 gms) in toluene (100 ml) was stirred at reflux, with the water being collected in a Dean and Stark trap. After cooling, the solution was washed with water, 1N NaOH and water before drying over MgSO$_4$. Evaporation of the solvent left an oil (20.17 gms) which was dissolved in EtOH (70 ml). After standing for 1 hour the cream precipitate was filtered off and dried in vacuo (10.44 gms).

c. To a solution of NaOMe (5.1 gms) in ethanol (75 ml) was added guanidine hydrochloride (8.2 gms). After stirring for 30 minutes the NaCl was filtered off, the above acetal added and the mixture stirred at reflux for 1 hour. The solvent was then concentrated and the product filtered off. Recrystallisation from ethanol gave the product as a white solid, 7.67 gms, 70% yield, mp. 212.5°–214° C.

The diamino-pyrimidine (6.12 gms) was dissolved in ethanol (250 ml), concentrated hydrochloric acid (2.07 ml) added, and the suspension chilled for 2 hours. The precipitate was then filtered off and dried to give the hydrochloride salt, 5.52 gms.

EXAMPLE 21B a. 2,3-Dichlorophenylacetic acid

Concentrated hydrochloric acid (100 ml) was poured onto crushed ice (150 ml), the solution added to 2,3-dichlorophenylacetonitrile (30.6 gms), and the mixture refluxed for 3 hours. After cooling, the mixture was diluted with water (500 ml), extracted with EtOAc (600 ml) and the organic phase washed with brine before drying over $MgSO_4$. Evaporation of the solvent left a white solid, 31.3 gms.

b. Ethyl 2,3-dichlorophenylacetate

To a suspension of the acid in ethanol (200 ml) was added concentrated $H_2SO_4$ (1 ml) and the mixture stirred at reflux for 3 hours. After cooling, the solvent was evaporated and the residue treated with concentrated $NH_4OH$ (3 ml) in water (50 ml). The organic phase was extracted into $CH_2Cl_2$, dried over $MgSO_4$, and the solvent evaporated to leave a clear liquid, 19.88 gms.

c. Ethyl-2-(2,3-dichlorophenyl)-3-N-morpholino-acrylate

To a mixture of the ester, morpholine (40.7 gms) and ethyl orthoformate (69.24 gms) was added acetic anhydride (0.5 ml) and the resulting pale yellow solution stirred at reflux for 3 hours. After cooling, the mixture was concentrated in vacuo. A white precipitate started to form, and this was filtered off before further concentrating the filtrate to give a brownish clear oil. Standing overnight in vacuo gave a yellow solid, 34.34 gms.

d. 5-(2,3-dichlorophenyl)isocytosine

To the above ester was added guanidine hydrochloride (26.6 gms) slurried in sodium 2-methoxyethoxide (from 6.6 gms of Na) in 2-methoxyethanol (150 ml), and the mixture stirred at reflux overnight. After cooling, the mixture was concentrated in vacuo, diluted with water (100 ml) and then washed with $Et_2O$ (200 ml). The aqueous phase was acidified with AcOH, and the precipitate filtered off and washed with EtOH and then $Et_2O$ before drying in vacuo, 13.48 gms.

e. $N^1$-[4-chloro-5-(2,3-dichlorophenyl)-2-pyrimidinyl]-$N^2,N^2$-dimethylformamidine To a mixture of the above isocytosine (14.4 gms) in $CH_2Cl_2$ (200 ml) was added dropwise during 30 minutes fresh Vilsmeier-Haack reagent (from 2.75 equivalents of $SOCl_2$ and 2.58 equivalents of DMF), and the mixture refluxed for 6 hours. After cooling, 1N NaOH (250 ml) was added slowly. The aqueous phase was washed with $CH_2Cl_2$ and the combined organic extracts washed with brine before drying over $MgSO_4$. Evaporation of the solvent and chromatography on $SiO_2$ gel, eluting with EtOAc gave 13.6 gms, mp. 113°–115° C.

f. 2-Amino-4-chloro-5-(2,3-dichlorophenyl)pyrimidine

To the formamidine in EtOH (50 ml) was added ethanolic $MeNH_2$ (8 equiv.) in EtOH (50 ml), and the mixture sealed in a Parr reaction vessel before stirring at room temperature for 5 hours. The reaction mixture was then concentrated in vacuo, the residue mixed with 1N NaOH (75 ml), filtered, washed with water and dried in vacuo, 11.2 gms, mp. 228°–30° C.

g. 2,4-Diamino-5-(2,3dichlorophenyl)pyrimidine

To 2-amino-4-chloro-5-(2,3-dichlorophenyl)pyrimidine (6.73 gms) was added ethanolic ammonia (30 equiv. in 50 ml EtOH) and the mixture sealed in a Parr reaction vessel and heated to 125° C. for 38 hours. After cooling, the mixture was concentrated in vacuo and the residue mixed with 1N NaOH (75 ml), filtered, washed with water and dried in vacuo, 6.14 gms, mp. 208°–211° C.

EXAMPLE 22

Synthesis of 2,4-Diamino-5-(2-chlorophenyl)-6-methyl-pyrimidine

This compound was prepared according to JACS, (1951), 73, 3763-70, mp. 225° C.

EXAMPLE 23

Synthesis of 2,4-Diamino-5-(2-chlorophenyl)pyrimidine

This compound was prepared according to JACS, (1951, 73, 3763-70, mp. 125°–8° C.

EXAMPLE 24

Synthesis of 2,4-Diamino-5-(2-chlorophenyl)-6-ethylpyrimidine

Prepared as for Example 22, except that ethyl propionate replaced ethyl acetate. mp. 197°–8° C.

EXAMPLE 25

Synthesis of 2,4-Diamino-5-(2,4-dichlorophenyl)-6-trifluoromethylpyrimidine

This compound was prepared in a manner analogous to the compound of Example 14 from 2,4-dichlorophenylacetonitrile (Aldrich): mp. 220.5°–221° C.

EXAMPLE 26

Synthesis of 6-Benzyloxymethyl-2,4-diamino-5-(2,4-dichlorophenyl)pyrimidine

This compound was prepared in a manner analogous to the compound of Example 16 from 2,4-dichlorophenylacetonitrile and ethyl benzyloxyacetate, 3.77 gms, mp. 171°–172° C.

EXAMPLE 27

2-(4-methylpiperazin-1-yl)-4-amino-5-(2,4-dichlorophenyl)pyrimidine

A) A solution of 55.7 g (0.4equiv) of S-methylisothiourea sulphate in 280 ml of water was prepared and gently heated on a steam bath with stirring. Then 40 g (0.4 mol) of N-methyl-piperazine was slowly dripped into the solution while sweeping the flask out with nitrogen. The evolved gases were collected in several portions of a solution of 132 g of mercuric chloride in 400 ml of ethanol, which caused evolved methylmercaptan to be precipitated as methylmercuric chloride. After the addition of the N-methylpiperazine was complete, the reaction was continued until no more methylmercuric chloride precipitated. The reaction mixture was then concentrated in vacuo and chilled which caused the N-methyl-N'-amidinopiperazine sulphate to crystallise; 50.79 g was collected.

B) A mixture of 76.3 g (0.356 mol) of α-formyl-2,4-dichlorophenyl-acetonitrile, 63.7 g of isoamyl alcohol, 0.36 g of p-toluenesulphonic acid, 895 ml of toluene, and 10 drops of concentrated sulphuric acid were heated under reflux for 20 hours in the presence of a Dean and Stark trap to remove water formed in the reaction. Then an equal portion of i-amyl alcohol and a few drops of sulphuric acid were added, and the reaction was heated for another 20 hours, until the theoretical amount of water had been collected. The solution was cooled.

C) An 8.2 g portion of sodium was dissolved in 500 ml of absolute ethanol, and 50 g of N-methyl-N'-amidinopiperazine sulphate was added. The mixture was allowed to stir for 10 minutes. This was then added to solution B. The mixture was refluxed with stirring for 6 hours, allowed to stand

23 overnight and the solvent removed in vacuo. The residue was then extracted with dilute hydrochloric acid, which dissolved most of it. The solution was extracted three times with ether, followed by neutralization of the aqueous fraction, which precipitated a gum which solidified upon standing overnight; weight 30 g. This was crystallised repeatedly from 50% ethanol with the aid of decolourising charcoal. Very slow cooling was required in order for crystals to be formed; mp. 137° C.

Anal. Calcd for $C_{15}H_{17}Cl_2N_5$; C, 53.27; H, 5.07; N, 20.71; Found: C, 53.58; H, 5.14; N, 20.40.

EXAMPLE 28

Synthesis of 2,4-Diamino-5-(2,5-dichlorophenyl)-6-trifluoromethylpyrimidine

This compound was prepared in a manner analogous to the compound in Example 14 from 2,5-dichlorobenzyl alcohol (Lancaster Synthesis, 48.26 g) to give the title compound in a yield of 3.85 gms, mp. 215°–217° C.

EXAMPLE 29

Preparation of 2,4-Diamino-5-(2,3,5-trichlorophenyl) Pyrimidine

Guanidine hydrochloride (3.20 g) was added to a solution of sodium ethoxide (from 848 mg sodium) in ethanol (52 ml). The resulting white suspension was stirred at room temperature for 10 minutes. The enol ether from Example 3.2 (4.40 g) was added and the resulting mixture stirred at reflux for 3.5 hours. After cooling, the suspension was filtered, and the filtrate evaporated to dryness in vacuo. Chromatography on silica gel eluting with $CHCl_3$ to 3% $MeOH-CHCl_3$ gave the desired product which was triturated with ether and dried in vacuo. Yield=2.01 g, mp. 246°–249° C.

EXAMPLE 30

Synthesis of 4-Amino-5-(3-bromophenyl)-6-methyl-2-(4-methylpiperazin-1-yl) Pyrimidine To a solution of NaOEt (from 0.92 g of sodium) in ethanol (75 ml) was added 3-bromophenylacetonitrile (Aldrich, 7.85 g) and ethyl acetate (3.52 g). The mixture was heated under reflux for 6 hours. After cooling, the mixture was concentrated and the residue was dissolved in water. The aqueous phase was washed with ether, acidified with 2N HCl and extracted with ether. The extracts were bulked, dried ($MgSO_4$) and evaporated, 3.8 g, mp. 97°–103° C.

The resulting ketone (3.7 g), ethylene glycol (5 ml) and p-toluene-sulphonic acid (100 mg) were heated under reflux in toluene (100 ml) in a Dean & Stark apparatus for 3.5 hours. The mixture was cooled, concentrated and water was added to the residue. The product was extracted with ether and the extracts were bulked, dried ($MgSO_4$) and evaporated, 4.03 g, mp. 68°–71° C.

To a solution of NaOEt (from 0.28 g of sodium) in ethanol (30 ml) was added N-methylpiperazinoformamidine hydriodide (2.7 g). After stirring for 10 minutes, the ketal (1.41 g) was added and the mixture was stirred at reflux for 4 hours. After cooling the suspension was filtered, and the filtrate was concentrated. The residue was purified by chromatography on $SiO_2$ gel, eluting with 10% $MeOH/CHCl_3$ to give the desired product, 0.48 g, mp. 120°–122° C.

24

EXAMPLE 31

Synthesis of 2,4-Diamino-5-(1-naphthyl)-6-trifluoromethylpyrimidine

This compound was prepared in a manner analogous to the compound in Example 14 from 1-naphthylacetonitrile (Aldrich, 10 gms), to give the title compound in a yield of 0.69 gms, mp. 224°–226° C.

EXAMPLE 32

Preparation of 2-Amino-5-(2,4-dichlorophenyl)-4,6-dichloropyrimidine

1. Ethyl 2,4-dichlorophenylacetate 2,4-Dichlorophenylacetonitrile (27.9 g, 150 m.mol) was suspended in 2N NaOH (400 ml) and the mixture refluxed for 4 hours. The cooled reaction mixture was extracted with ether (2×200 ml) acidified to pH3 and the solid filtered and dried (22 g, 70%).

The product (20 g) was dissolved in EtOH (300 ml) and concentrated $H_2SO_4$ (5 ml) added carefully. The mixture was refluxed for 7 hours. The cooled reaction mixture was evaporated under reduced pressure and the residue partitioned between $CH_2Cl_2$ and water (30 ml each). The organic layer was extracted with saturated $NaHCO_3$ solution (200 ml), washed with water (100 ml), dried and evaporated in vacuo to give ethyl 2,4-dichlorophenylacetate as an oil (22.2 g, 89.5%).

2. Diethyl 2,4-Dichlorophenyl malonate

Sodium (1.86 g, 0.081M) was added in portions to absolute ethanol (150 ml) with stirring. After all the sodium had dissolved a solution of ethyl 2,4-dichlorophenylacetate (20 g) in diethyl carbonate (50 ml) was added dropwise. The reaction mixture was heated until EtOH distilled over. The rate of addition was controlled such that it equalled the rate of distillation. After the completion of addition the reaction mixture was heated and distilled for further 4 hours. The cooled reaction mixture was partitioned between water (300 ml) and EtOAc (300 ml) and the organic layer dried and evaporated in vacuo to give a yellow oil (21 g, 85%).

3. 2-Amino-5-(2,4-dichlorophenyl)-4,6-dihydroxypyrimidine

Sodium (4.52 g, 0.196M) was added in portions to ethanol (150 ml). After all the sodium had dissolved guanidine hydrochloride (12.44 g, 0.13M) was added followed by diethyl 2,4-dichlorophenyl malonate(20 g, 0.0655M). The mixture was refluxed for 6 hours, EtOH was removed under reduced pressure and the residue partitioned between 2N NaOH (400 ml) and EtOAc (400 ml). The aqueous layer was acidified with concentrated hydrochloric acid with cooling and the precipitated solid was filtered and dried (11 g, 62%).

4. 2-Amino-5-(2,4-dichlorophenyl) -4,6-dichloropyrimidine

A mixture of 2-amino-5-(2,4-dichlorophenyl)-4,6-dihydroxypyrimidine (10 g), phosphoryl chloride (100 ml) and dimethylaniline (1.5 ml) was refluxed for 6 hours. The cooled reaction mixture was carefully added to crushed ice and the insoluble solid was filtered and washed with 2N HCl, followed by water. The solid was resuspended in water, neutralised (0.88 $NH_4OH$) with cooling, and the mixture stood overnight at room temperature. The insoluble solid was filtered, dried and purified by flash column chromatography to give the title compound (2.5 g, 22%), mp. 211°–213° C. Microanalysis:

EXAMPLE 33

Synthesis of 2,4-Diamino-6-chloro-5-(2,4-dichlorophenyl)-pyrimidine

A mixture of 2-amino-5-(2,4-dichlorophenyl)-4,6-dichloropyrimidine (0.5 g) (Example 32) EtOH saturated with ammonia (20 ml) and copper powder (0.05 g) was heated in an autoclave at 180° C. for 18 hours. The cooled reaction mixture was filtered, evaporated and the residue purified by flash column chromatography to give the title compound (0.12, 25%), mp. 219° C. Microanalysis:

Calcd: C, 40.82; H, 2.55; N, 19.05; Found: C, 41.27; H, 2.46; N, 18.74.

EXAMPLE 34

Synthesis of 2-Amino-4-chloro-5-(2,4-dichlorophenyl)-6-methylthiopyrimidine

A mixture of 2-amino-5-(2,4-dichlorophenyl)-4,6-dichlorohyrimidine (0.5 g) (Example 32) THF (15 ml), methanethiol sodium salt (0.113 g), copper powder (0.05 g) and tris[2-(2-methoxyethoxy) ethyl]amine (0.1 g) was heated in an autoclave at 180° C. for 18 hours. The cooled reaction mixture was filtered, evaporated and the residue purified by flash column chromatography to give the title compound (0.262 g, 52%), mp. 201°–202° C. (softens at 196° C.). Microanalysis:

Calcd: C, 41.19; H, 2.50; N, 13.10; Found: C, 41.10; H, 2.52; N, 12.77.

EXAMPLE 35

Synthesis of 2,4-Diamino-5-(2,4-dichlorophenyl)-6-methylthiopyrimidine

A mixture of 2-amino-4-chloro-5-(2,4-dichlorophenyl)-6-methylthio pyrimidine (0.5 g) (Example 32) EtOH saturated with ammonia (20 ml), copper powder (0.05 g) and tris[2-(2-methoxyethoxy)ethyl]amine (0.01 g) was heated in an autoclave at 180° C. for 18 hours. The cooled reaction mixture was filtered, evaporated and the residue purified by flash column chromatography to give the title compound (0.11 g, 23.5%), mp. 191°–192° C. Microanalysis:

Calcd: for 0.2 hydrate: C, 43.33; H, 3.41; N, 18.38; Found: C, 43.37; H, 3.23; N, 18.33.

EXAMPLE 36

4-Amino-5-(3,5-dichlorophenyl)-6-methyl-2-(4-methylpiperazin-1-yl)pyrimidine a. 3,5-Dichlorophenylacetonitrile A mixture of 3,5-dichlorobenzyl alcohol (Aldrich, 25 g), thionyl chloride (100 ml) and DMF (0.5 ml) was stirred and refluxed for 4 hours. After cooling the mixture was concentrated in vacuo, the residue was taken up in ether, washed with saturated aqueous NaHCO₃ and brine, dried (MgSO₄) and concentrated in vacuo to give 3,5-dichlorobenzyl chloride as a light yellow solid, which was used without further purification, 28 g, mp. 32°–36° C.

To a vigorously stirred solution of 3,5-dichlorobenzylchloride (28 g) in dichloromethane (150 ml) was added a mixture of KCN (27.5 g) and tetrabutylammonium hydrogen sulphate (2.38 g) in water (110 ml). After stirring at room temperature for 22 hours, the mixture was diluted with dichloromethane, the organic phase washed with water and concentrated in vacuo to leave an oil. Filtration through silica with toluene followed by concentration then trituration with hexane gave the desired product as a colourless solid. 15.8 g, mp. 31°–32° C.

b. 4-Amino-5-(3,5-dichlorophenyl)-6-methyl-2-(4-methylpiperazin-1-yl)pyrimidine

To a stirred solution of NaOEt (from 0.69 g sodium), in ethanol (25 ml) at reflux, was added over 5 minutes a mixture of 3,5-dichlorophenylacetonitrile (9.3 g) and ethyl acetate (3.3 g) in dry dimethoxyethane (10 ml). After stirring at reflux for 4 hours, the mixture was cooled on ice, acidified with acetic acid, poured into cold water and extracted with dichloromethane. The combined extracts were washed with water and concentrated to give an oil. Trituration with hexane gave 2-(3,5-dichlorophenyl)-3-oxobutyronitrile as a colourless solid (4.15 g).

To a solution of the acyl acetonitrile (4.1 g) in ether (100 ml) was added in portions an excess of a solution of diazomethane in ether. After stirring for 2 hours at room temperature the solution was concentrated in vacuo to give the enol ether. To a stirred solution of NaOEt (from 0.72 g sodium) in ethanol (25 ml) was added N-methylpiperazinoformamidine hydriodide (7.29 g). After 10 minutes a solution of the above enol ether in ethanol (25 ml) was added and then stirred and refluxed for 4.5 hours. After cooling the solvent was evaporated in vacuo and the residue shaken with 2N NaOH (50 ml). The solid was filtered off, washed with water, dried in air and chromatographed (silica; 1:9 MeOH:CHCl₃) to give the desired product as a colourless solid, 1.6 g, mp. 164°–166° C.

EXAMPLE 37

Preparation of 2,4-Diamino-5-(2,5-dichlorophenyl)-6-methylpyrimidine

This compound was made in an analogous manner to the compound of Example 6 from 2,5-dichlorobenzylalcohol (Lancaster Synthesis). Mp. 226°–228° C.: TLC (SiO₂: CHCl₃/MeOH, 9:1) Rf=0.24.

EXAMPLE 38

Preparation of 2,4-Diamino-5-(3,4-dichlorophenyl)-6-trifluoromethylpyrimidine

This compound was made in an analogous manner to the compound of Example 4, from 3,4-dichlorophenylacetonitrile (Aldrich) mp. 252°–254.5° C.: TLC (SiO₂; methanol/chloroform, 1:9) Rf=0.38.

EXAMPLE 39

Preparation of 2,4-Diamino-5-(2,3-dichlorophenyl-4-nitrophenyl)pyrimidine

This compound was made in an analogous manner to the compound of Example 5 from 2,4-diamino-5-(2,3-dichlorophenyl)pyrimidine (Example 21). The reaction gave a mixture of the 4-nitro and 5-nitro derivatives from which the title compound was separated by column chromatography (SiO₂, EtOAc), mp. 237°–9° C. Also separated in this Calcd: C, 38.83; H, 1.6; N, 13.59; Found: C, 38.59; H, 1.53; N, 13.40.

manner was 2,4-diamino-5-(2,3-dichloro-5-nitrophenyl)pyrimidine, mp. 264°–6° C.

EXAMPLE 40

Preparation of 2,4-Diamino-5-(2,4,-dichlorophenyl)-6-(diethoxymethyl)pyrimidine

This compound was prepared in a manner analogous to 2,4-diamino-5-(2,3-dichlorophenyl)-6-(diethoxymethyl)pyrimidine (Example 18.1) from 2,4-dichlorophenylacetonitrile, mp. 225° C.

EXAMPLE 41

Preparation of 2,4-Diamino-5-(3,5-dichlorophenyl)-6-methylpyrimidine

This compound was prepared in a manner analogous to the compound of Example 6 from 3,5-dichlorophenylacetonitrile (Aldrich). mp. 242°–244° C.

EXAMPLE 42

Preparation of 2,4-Diamino-5-(2.3-dichlorophenyl)-6-trifluoromethylpyrimidine N-oxide This compound was made from the compound of Example 14 by reaction with MCPBA in CHCl$_3$ at room temperature. Mp. 275°–278° C.

EXAMPLE 43

Preparation of 2,4-Diamino-5-(2,3-dichlorophenyl)-6-tribromomethylpyrimidine

This compound was prepared from the compound of Example 15 by reaction with excess bromine and sodium acetate in acetic acid at reflux. The title compound was separated from a mixture with the compound of Example 75 by coloumn chromatography, mp. 210° C. (dec).

EXAMPLE 44

Preparation of 2.4-Diamino-5-(2.4-dichlorophenyl)-6-methoxymethylpyrimidine

This compound was prepared in a manner analogous to Example 2, from 2,4-dichlorophenylacetonitrile, mp. 183°–185° C. Single spot on TLC.

EXAMPLE 45

Preparation of 2,4-Diamino-5-(2,6-dichlorophenyl)-6-methylpyrimidine

This compound was prepared in a manner analogous to Example 6 from 2,6-dichlorophenylacetonitrile (Aldrich) , mp. 250° C.

EXAMPLE 46

Preparation of 2,4-Diamino-5-(2,4-dichlorophenyl)pyrimidine-6-carboxaldehyde

This compound was made from the compound of Example 40 in an analogous manner to the compound of Example 18.2, mp. >350° C.

EXAMPLE 47

Preparation of 2,4-Diamino-5-(2,3-dichloro-4-nitrophenyl)-6-methylpyrimidine

This compound was made from the compound of Example 15 in an analogous manner to the compound of Example 3 g, mp. 265° C. Also obtained from this reaction was 2,4-diamino-5(2,3-dichloro-5-nitrophenyl)-6-methylpyrimidine.

EXAMPLE 48

Preparation of 2,4-Diamino-5-(2,4-dichlorophenyl)-6-hydroxyliminomethylpyrimidine This compound was made from the compound of Example 46 by reaction with hydroxylamine hydrochloride in ethanol, mp. 260°–5° C.

EXAMPLE 49

Preparation of 2.4-Diamino-5-(2,4-dichlorophenyl)-6-hydroxymethylpyrimidine

This compound was made from the compound of Example 46 in an analogous manner to the compound in Example 18.3, mp. 169°–171° C.

EXAMPLE 50

Preparation of 2,4-Diamino-5-(2,3,4-trichlorophenyl)-6-methylpyrimidine

This compound was made from the compound of Example 47 by reduction to the amine (PtO$_2$, H$_2$, AcOH), formation of the diazonium salt (NaNO$_2$, H$_2$SO$_4$), and reaction of this with CuCl (as for Example 57). Sublimes at 275° C. Homogenous on TLC (methanol/chloroform, 1:9) Rf=0.36.

EXAMPLE 51

2,4-Diamino-5-(2,6-dichlorophenyl)-6-methoxymethyl-pyrimidine

This compound was prepared in an analogous manner to the compound of Example 2 from 2,6-dichlorophenylacetonitrile (Aldrich), mp. 204°–207° C.

EXAMPLE 52

Preparation of 2,4-Diamino-5-(2,3,5-trichlorophenyl)-6-trichloromethyl Pyrimidine This compound was made from the compound of Example 6 by reacting with NCS in AcOH at 100° C. (AIBN as catalyst), mp. 226°–227° C.

EXAMPLE 53

2,4-Diamino-5-(2,4-dichlorophenyl)-6-fluoromethylpyrimidine 1. 2,4-Diamino-6-bromomethyl-5-(2,4-dichlorophenyl)pyrimidine 2,4-Diamino-6-benzyloxymethyl-5-(2,4-dichlorophenyl)pyrimidine (Example 26) (6.5 g) was dissolved in a 474 solution of hydrobromic acid in acetic acid (75 ml) and the mixture stirred and heated at 100° C. for 6 hours. After standing at room temperature overnight the dihydrobromide salt was filtered off, washed with ether and dried in vacuo, 6 g. To a stirred solution of the dihydrobromide salt (0.43 g) in dimethylsulphoxide (4 ml) was added dropwise a solution of sodium bicarbonate (0.84 g) in water (10 ml) . After 30 minutes the precipitate was filtered off, washed with water then ether and dried in vacuo, 0.26 g, mp.>270° C. (decomposes).

2. 2,4-Diamino-5-(2,4-dichlorophenyl)-6-fluoromethylpyrimidine

To a solution of 2,4-diamino-6-bromomethyl-5-(2,4-dichlorophenyl) pyrimidine (1.04 g) in tetramethylene sulphone (4.5 ml) was added cesium fluoride (1 g). The mixture was stirred and heated at 100° C. for 4 hours, cooled, diluted with water and extracted with chloroform. The combined extracts were washed with water, dried ($MgSO_4$) and concentrated in vacuo. The residue was chromatographed (silica; 19:1:0.1 dichloromethane/methanol/triethylamine) to give the title compound, which was recrystallised from ethanol. 0.19 g, mp. 210°–211° C.

EXAMPLE 54

Preparation of 2,4-Diamino-5-[2-chloro-5-(N,N-dimethylsulphamoyl)phenyl]-6-methylpyrimidine 1. 2,4-Diamino-5-(2-chloro-5-nitrophenyl)-6-methylpyrimidine To a solution of 2,4-diamino-5-(2-chlorophenyl)-6-methyl pyrimidine (11.84 g) (Example 22) in concentrated $H_2SO_4$ (100 ml), was added potassium nitrate (5.1 g). After stirring at room temperature for 90 minutes, the solution was poured onto ice and basified with 10N NaOH. The product was extracted with ethyl acetate, bulked, dried ($MgSO_4$) and evaporated, 13.9 g, 236°–240° C.

2. 2,4-Diamino-5-(5-amino-2-chlorophenyl)-6-methylpyrimidine

A solution of 2,4-diamino-5-(2-chloro-5-nitrophenyl)-6-methyl pyrimidine (13.9 g) in acetic acid (500 ml) was reduced under an atmosphere of hydrogen in the presence of $PtO_2$ (0.28 g). The mixture was filtered through hyflo and the filtrate was concentrated. The residue was neutralised with saturated $NaHCO_3$ solution and the product was extracted with ethyl acetate, bulked, dried ($MgSO_4$) and evaporated. Chromatography on $SiO_2$gel, eluting with $CHCl_3$ to 40% MeOH/$CHCl_3$, gave the desired product, 6 g, mp. 117°–121° C.

3. 2,4-Diamino-5-(2-chloro-5-N,N-dimethylsulphamoylphenyl)-6-methylpyrimidine 2,4-Diamino-5-(5-amino-2-chlorophenyl)-6-methylpyrimidine (0.25 g) was dissolved in water (0.8 ml) and concentrated HCl (0.5 ml). To the cooled solution (below 10° C.) was added a solution of sodium nitrite (0.07 g) in water (0.5 ml). After stirring at room temperature for 2 hours, the solution was cooled to 5° C. Cupric chloride (0.05 g) and 5.14M $SO_2$ in acetic acid (0.97 ml) were added and the reaction was stirred at 5° C. overnight. The mixture was filtered and washed with water to give the sulphonyl chloride, 0.23 g.

The sulphonyl chloride (0.16 g) was dissolved in THF (2 ml) aqueous dimethylamine (2 ml) was added. After stirring overnight, the solution was diluted with water, extracted with ethyl acetate, bulked, dried ($MgSO_4$) and evaporated. Chromatography on $SiO_2$ gel, eluting with 2% MeOH/$CHCl_3$, gave the desired product, 0.047 g, mp. 283°–285° C.

EXAMPLE 55

Preparation of 2,4-Diamino-(3.5-dichlorophenyl)-6-methoxymethylpyrimidine

This compound was prepared in an analogous manner to the compound in Example 2 from 3,5-dichlorophenylacetonitrile, mp. 228°–230° C.

EXAMPLE 56

Preparation of 2,4-Diamino-5-(2,3-dichlorophenyl)-6-hydroxypyrimidine

1. Ethyl-2-cyano-2-(2,3,-dichlorophenyl) acetate Sodium (1.2 g) was added portionwise to ethanol (50 ml) with stirring. After the sodium had dissolved a solution of 2,4-dichlorophenylacetonitrile (9.4 g) in diethylcarbonate (25 ml) was added dropwise. The reaction mixture was heated until EtOH distilled over. The rate of addition was controlled such that it equalled the rate of distillation. After the completion of the addition, the reaction mixture was heated and distilled for a further 4 hours. The cooled reaction mixture was partitioned between water and EtOAc (300 ml each). The organic layer was dried and evaporated in vacuo and the residue was purified by flash column chromatography to give the title product. (5 g, 39%).

2. 2,4-Diamino-5-(2,3-dichlorophenyl)-6-hydroxypyrimidine

Sodium (1.2 g, 0.052 mol) was added in portions to absolute ethanol (50 ml) with stirring. After the sodium had dissolved guanidine hydrochloride (3.69 g, 0.039 mol) was added followed by ethyl-2-cyano-2-(2,3-dichlorophenyl)acetate (5 g, 0.0195 mol). The mixture was refluxed for 8 hours, EtOH was removed under reduced pressure and the residue was partitioned between EtOAc and water. The EtOAc layer was extracted with 2N NaOH and the extract was neutralised with 2N HCl with cooling. The precipitated solid was filtered and dried to give the title compound. (0.22 g), mp. 275° C. (decomp). Microanalysis:

Calcd. for 0.25 hydrate: C, 43.56; H, 3.09; N, 20.33; C, 43.76; H, 3.09; N, 20.03.

EXAMPLE 57

Synthesis of 2,4-Diamino-5-(2,4,5-trichlorophenyl)-6-methylpyrimidine a. Preparation of 2-(2,4-dichlorophenyl)-3-oxo-butyronitrile A solution of 2,4-dichlorophenylacetonitrile (30.00 gms, 161 mmol) (Aldrich) in dry ethyl acetate (36 ml) was added dropwise to an ethanolic solution of sodium ethoxide, prepared in situ from sodium metal (4.90 g, 213 mmol) and dry ethanol (60 ml). This reaction mixture was refluxed for two hours, allowed to stand overnight at room temperature and the ethanol was evaporated. The yellow solid obtained was dissolved in water and the resulting solution was extracted twice with ether. The aqueous layer was chilled and acidified with hydrochloric acid. The crude product was extracted with ether to give 23.31 g of white solid.

b. Preparation of 2,4-diamino-5-(2,4-dichlorophenyl)-6-methylpyrimidine

A solution of crude 2-(2,4-dichlorophenyl)-3-oxo-butyronitrile (23.24 g) in dry toluene (400 ml) was refluxed with ethylene glycol (280 ml) and p-toluenesulphonic acid (8.00 g, 42 mmol) for four hours using a Dean and Stark trap. After cooling, the organic phase was washed with saturated NaHCO₃, dried over MgSO₄, and the solvent evaporated to leave a solid (24.0 gm).

Finely ground guanidine hydrochloride (19.1 g, 200 mmol) was added to an ethanolic solution of sodium ethoxide, prepared in situ from sodium metal (5.0 g, 218 mmol) in dry ethanol (500 ml). A solution of the ketal (25.0 g, 92 mmol) in dry ethanol (10 ml) was added to the guanidine solution. This mixture was refluxed for two hours and allowed to stand overnight at room temperature. The ethanol was evaporated and the crude product recrystallised from hot acetone to give 17.23 g of product, mp. 222°–222.5° C.

c. Preparation of 2,4-Diamino-5-(2,4-dichloro-5-nitrophenyl)-6-methylpyrimidine

Finely ground potassium nitrate (6.5 g 64 mmol) was added to a solution of 2,4-diamino-5-(2,4-dichlorophenyl)-6-methyl pyrimidine (17.23 g, 64 mmol) in concentrated sulphuric acid (150 ml). This mixture was stirred at room temperature for 90 minutes. The reaction mixture was then added to sodium bicarbonate and ice. The product was extracted with ethyl acetate. After the ethyl acetate was removed, a yellow solid was obtained (30.86 g). A portion of this crude product (7.0 g) was passed through a silica flash chromatography column and eluted with ethyl acetate to give the pure product (4.81 g).

d. Preparation of 2,4-Diamino-5-(5-amino-2,4-dichlorophenyl)-6-methylpyrimidine 2,4-diamino-5-(2,4-dichloro-5-nitrophenyl)-6-methylpyrimidine (4.80 g, 15mmol) was dissolved in glacial acetic acid (18 ml). This solution and 10 mg of Adam's catalyst was stirred under an atmosphere of hydrogen at room temperature for 4 hours. The catalyst was filtered off and the acetic acid was evaporated. The colourless liquid obtained was dissolved in ethyl acetate and washed 3 times with water. After evaporating the ethyl acetate, a white solid was obtained (2.64 g, 9 mmol).

e. Preparation of 2,4-Diamino-5-(2,4,5-trichlorophenyl)-6-methylpyrimidine 2,4-diamino-5-(5-amino-2,4-dichlorophenyl)-6-methylpyrimidine (1.95 g, 7 mmol) was dissolved in a mixture of concentrated hydrochloric acid (3.6 ml) and water (6 ml). The temperature was lowered to 10° C. A chilled aqueous solution (3.6 ml) of sodium nitrite (0.50 g, 7 mmol) was added dropwise, keeping the temperature at 10° C. This mixture was stirred at room temperature for 2 hours, then chilled before adding it dropwise to a cold solution of cuprous chloride (1.7 g, 17 mmol) in concentrated hydrochloric acid (50 ml). A grey solid precipitated which was filtered off and dried. This crude product (2.30 g) was dissolved in ethyl acetate and washed twice with ammonium hydroxide solution and once with brine. After evaporating the ethyl acetate an off-white solid was obtained (2.04 g). After recrystallisation from 104 methanol in chloroform the pure product was obtained (0.55 g, 2 mmol), mp. 262° C. (dec).

EXAMPLE 58

Synthesis of 4-amino-2-(ethylamino)-5-(2,3,5-trichlorophenyl) pyrimidine

To a solution of NaOEt (from 0.1 g of sodium) in ethanol (10 ml) was added ethylguanidine sulphate (1 g) (Aldrich). After stirring for 10 minutes, the enol ether (Example 3.2) (0.486 g) was added and the mixture was stirred at reflux for 4 hours. The reaction was left standing at room temperature overnight and then filtered. The filtrate was concentrated and the residue was purified by chromatography on SiO₂ gel, eluting with CHCl₃ to give the desired product, 0.11 g, mp. 149°–152° C.

EXAMPLE 59

2.4-Diamino-5-(2,4-dichlorophenyl)-6-cyanomethyl-pyrimidine

This compound was prepared from 2,4-diamino-5-(2,4-dichlorophenyl)-6- bromomethyl-pyrimidine (Example 53) by reaction with sodium cyanide in DMF at room temperature, mp. 249°–251° C.

EXAMPLE 60

2,4-Diamino-5-(2,4-dichlorophenyl)-6-dimethylaminomethyl Pyrimidine

This compound was prepared from 2,4-diamino-5-(2,4-dichlorophenyl)-6-bromomethyl-pyrimidine (Example 53) by reaction with dimethylamine in ethanol at room temperature, mp. 170°–172° C.

EXAMPLE 61

2,4-Diamino-5-(2,4-dichlorophenyl)-6-cyanopyrimidine

This compound was prepared from the compound of Example 48 by reaction with trifluoroacetic anhydride in pyridine, mp. 249° C.

EXAMPLE 62

2.4-Diamino-5-(2-chloro-4-fluorophenyl)-6-methylpyrimidine

This compound was prepared in an analogous manner to the compound of Example 15 from 2-chloro-4-fluorophenylacetonitrile, which was itself prepared from 2-chloro-4-fluorotoluene (Aldrich, mp. 238° C.

EXAMPLE 63

2,4-Diamino-5-(3,4-dichlorophenyl)-6-methoxymethyl pyrimidine

This compound was prepared in an analogous manner to the compound of Example 2 from 3,4-dichlorophenylacetonitrile (Aldrich), mp. 204°–206° C.

EXAMPLE 64

2,4-Diamino-5-(2,3-dichlorophenyl)-6-ethylpyrimidine

This compound was prepared in an analogous manner to the compound of Example 15 from ethyl propionate, mp. 228°–230° C.

EXAMPLE 65

2,4-Diamino-5-(2,4-difluorophenyl)-6-methylpyrimidine

This compound was prepared in an analogous manner to the compound of Example 6 from 2,4-difluorophenylacetonitrile (Aldrich), mp. 291°–296° C.

EXAMPLE 66

2,4-Diamino-5-(2-naphthyl)-6-methylpyrimidine

This compound was prepared in an analogous manner to the compound of Example 6 from 2-naphthylacetonitrile (Aldrich), mp. 221°–222° C.

EXAMPLE 67

2,4-Diamino-5-(1-naphthyl)-6-methylpyrimidine

This compound was prepared in an analogous manner to the compound of Example 6 from 1-naphthylacetonitrile (Aldrich), mp. 224°–225° C.

EXAMPLE 68

2-Hydroxy-4-amino-5-(2,3-dichlorophenyl)pyrimidine

This compound was prepared from the compound of Example 21 by reaction with sodium nitrite in 1N $H_2SO_4$ at reflux to give a mixture of the title compound and the compound of Example 21B.d. The title compound was separated by column chromatography, mp. 330°–334° C.

EXAMPLE 69

2-Amino-4-ethoxy-5-(2,4-dichlorophenyl)-6-methylthiopyrimidine

This compound was made from the compound of Example 32.4 by reaction with methanethiol sodium salt in ethanol, mp. 123°–124° C.

EXAMPLE 70

2.4-Diamino-5-(2,3,5-trichlorophenyl)-6-hydroxymethylpyrimidine

This compound was made from the compound of Example 2 by reaction with trimethylsilyl iodide in sulpholane at 80° C., mp. 101°–105° C.

EXAMPLE 71

2.4-Diamino-5-(2,3,5-trichlorophenyl)-6-fluoromethylpyrimidine

This compound was prepared in an analogous manner to the compound of Example 18 from 2,4-diamino-5-(2,3,5-trichlorophenyl )-6-hydroxymethylpyrimidine, mp. 215°–217° C.

EXAMPLE 72

2,4-Diamino-5-(2,4-dichlorophenyl)-6-carbamoylpyrimidine

This compound was prepared from the compound of Example 61 by reaction with concentrated sulphuric acid at room temperature, mp. 298°–299° C.

EXAMPLE 73

2.4-Diamino-5-(2,4-dichlorophenyl) pyrimidine-6-carboxylic Acid

This compound was prepared from the compound of Example 46 reaction with potassium permanganate, mp. 227° C.

EXAMPLE 74

Ethyl-2,4-diamino-5-(2,4-dichlorophenyl) pyrimidine-6-carboxylate

This compound was prepared from the compound of Example 73 by refluxing in ethanol in the presence of concentrated sulphuric acid, mp. 177.5° C.

EXAMPLE 75

2,4-Diamino-5-(2,3-dichlorophenyl)-6-dibromomethylpyrimidine

This compound was prepared from the compound of Example 15 by reaction with 2 eq NBS in $CCl_4$ and AIBN as initiator. The title compound was separated from a mixture with the compound of Example 43 by column chromatography, mp. 270° C. (dec).

EXAMPLE 76

2-Dimethylamino-4-amino-5-(2,4-dichlorophenyl)pyrimidine

This compound was prepared in an analogous manner to the compound of Example 10 from 2,4-dichlorophenylacetonitrile (Aldrich), mp. 151° C.

EXAMPLE 77

2-Dimethyl amino-4-amino-5-(3,4-dichlorophenyl)-6-methylpyrimidine

This compound was made in an analogous manner to the compound of Example 13 from 3,4-dichlorophenylacetonitrile.

EXAMPLE 78

2-N-Piperidyl-4-amino-5(2,4-dichlorophenyl)pyrimidine

This compound was prepared in an analogous manner to the compound of Example 76 from 1-piperidinecarboxamidine sulphate (Bader), mp. 169° C.

EXAMPLE 79

2-Methylamino-4-amino-5-(2,3.5-trichlorophenyl)pyrimidine

This compound was prepared in an analogous manner to the compound of Example 58 from 1-methyl-guanidine hydrochloride (Aldrich), mp. 155°–157° C.

EXAMPLE 80

2,4-Diamino-5-(2-chloro-5-bromophenyl)-6-methylpyrimidine

This compound was prepared in a similar manner to the compound of Example 54 by reaction of the diazonium salt with cuprous bromide, mp. 212°–216° C.

EXAMPLE 81

2.4-Diamino-5-(2-chloro-5-iodophenyl)-
6-methylpyrimidine

This compound was prepared in a similar manner to the compound of Example 54 by reaction of the diazonium salt with potassium iodide, mp. 232°–234° C.

EXAMPLE 82

2,4-Diamino-5-(2-chloro-5-cyanophenyl)
-6-methylpyrimidine

This compound was prepared in a similar manner to the compound of Example 54 by reaction of the diazonium salt with cuprous cyanide, mp. 239°–241 ° C.

EXAMPLE 63

2,4-Diamino-5-(2-chloro-5-fluorophenyl)-
6-methylpyrimidine

This compound was prepared in a similar manner to the compound of Example 54 by way of the diazonium tetrafluoroborate salt, mp. 195°–197° C.

EXAMPLE 84

2,4-Diamino-5-(2-chloro-5-methylthiophenyl)-
6-methylpyrimidine

This compound was prepared in a similar manner to the compound of Example 54 by reaction of the diazonium salt with methanethiol in the presence of copper powder, mp. 194°–198° C.

EXAMPLE 85

2-Amino-4,6-di(methylthio)-
5-(2,4-dichlorophenyl)pyrimidine

This compound was prepared from the compound of Example 32.4 by reaction with methanethiol sodium salt in methanol in the presence of tris[2-(2-methoxyethoxy)ethyl] amine and copper powder, mp, 164°–165° C.

EXAMPLE 86

2,4-Diamino-5-(2-chloro-
5-methanesulphonylaminophenyl)-6-methylpyrimidine

This compound was prepared from 2,4-diamino-5-(2-chloro-5-aminophenyl)-6-methylpyrimidine from Example 54 by reaction with methanesulphonylchloride in pyridine, mp. 234°–240° C.

EXAMPLE 87

2,4-Diamino-5-(2,3-dichlorophenyl)-
1-methylpyrimidinium iodide

This compound was prepared from the compound of Example 21 and methyl iodide, mp. 280°–284° C.

EXAMPLE 88

2-Amino-4-methylamino-
5-(2,3-dichlorophenyl)pyrimidine

This compound was prepared in an analogous manner to the compound of Example 21B.g by reaction with methylamine in ethanol, mp. 233°–237° C.

EXAMPLE 89

2-Amino-4-dimethylamino-
5-(2,3dichlorophenyl)pyrimidine hydrochloride

This compound was prepared in an analogous manner to the compound of Example 21B.g by reaction with dimethylamine in ethanol and subsequent conversion to the hydrochloride salt, mp. 295°–300° C.

EXAMPLE 90

2-Amino-4-chloro-5-(2.4-dichlorophenyl)pyrimidine

The compound was prepared in an analogous manner to he compound of Example 21B.f. from 5-(2,4-dichlorophenyl)isocytosine, mp. 215°–216° C.

EXAMPLE 91

2-Amino-4-methylamino-
5-(2,4-dichlorophenyl)pyrimidine

This compound was prepared from the compound of Example 90 by reaction with methylamine in ethanol, mp. 189°–90° C.

EXAMPLE 92

2-Amino-4-dimethylamino-
5-(2,4-dichlorophenyl)pyrimidine Hydrochloride

This compound was prepared from the compound of Example 90 by reaction with dimethylamine in ethanol and subsequent conversion to the hydrochloride salt, mp. 297°–301° C.

EXAMPLE 93

2-Amino-4-piperidino-5-(2,4-dichlorophenyl)pyrimidine Hydrochloride

This compound was prepared from the compound of Example 90 by reaction with piperidine in ethanol and subsequent conversation to the hydrochloride salt, mp. 303° C. (dec).

Preferred among the compounds of formula (I) are the pyrimidines of the foregoing Examples 1,2,3,4,14 and 16. together with salts (in particular, pharmaceutically acceptable salts) thereof; these bases have the following respective two-dimensional structures.

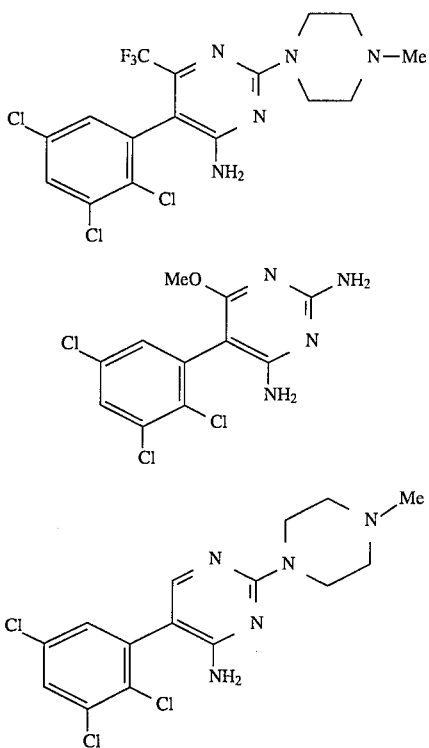

Example 1

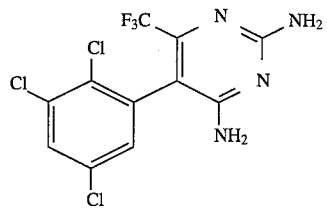

Example 4

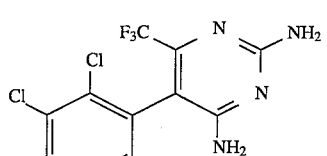

Example 14

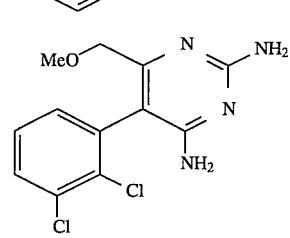

Example 2

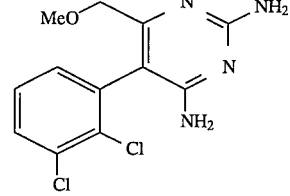

Example 16

Example 3

| | TABLE OF ¹H NMR DATA (δ) | |
|---|---|---|
| EXAMPLE NO. | SOLVENT | ASSIGNMENT |
| 1 | CDCl₃ | 7.56(d, 1H), 7.18(d, 1H), 4.65–4.50 (br.s, 2H), 3.88(t, 4H), 2.5(t, 4H), 2.36(s, 3H) |
| 2 | DMSO-d₆ | 3.06(s, 3H, —OMe), 3.8(d, 1H, J12.5Hz, —C$\underline{H}_2$OMe), 3.9(d, 1H, J12.5Hz, —C$\underline{H}_2$OMe), 5.98(br.s, 2H, —NH₂), 6.1(br.s, 2H, —NH₂), 7.32(d, 1H, J2.5Hz, 6'-H), 7.78(d, 1H, J2.5Hz, 4'-H) |
| 3 | DMSO-d₆ | 7.8(d, 1H), 7.65(s, 1H), 7.36(d, 1H), 6.33–6.23(brs, 2H), 3.68(t, 4H), 2.32(t, 4H), 2.2(s, 3H) |
| 4 | DMSO-d₆ | 6.40(s, 2H), 6.55(s, 2H), 7.35(s, 1H), 7.80(s, 1H) |
| 5 | DMSO-d₆ | 8.6(s, 1H), 7.49(s, 1H), 6.4–6.3(br.s, 2H), 6.25–6.15(br.s, 2H) |
| 6 | DMSO-d₆ | 1.70(s, 3H), 5.75(s, 2H), 5.90(s, 2H), 7.30(s, 1H), 7.75(s, 1H) |
| 7 | CDCl₃ | 7.55(d, 1H), 7.18(d, 1H), 4.75–4.58 (br.s, 2H), 3.9–3.7(m, 8H) |
| 8 | CDCl₃ | 7.55(d, 1H), 7.18(d, 1H), 4.56–4.50 (br.s, 2H), 3.2(s, 6H) |
| 9 | DMSO-d₆ | 7.79(d, 1H), 7.67(s, 1H), 7.36(d, 1H), 6.47–6.27(br.s, 2H), 3.72–3.57(m, 8H) |
| 10 | DMSO-d₆ | 7.78(d, 1H), 7.64(s, 1H), 7.35(d, 1H), 3.08(s, 6H) |
| 11 | CDCl₃ | 7.51(d, 1H), 7.17(d, 1H), 4.40–4.22 (br.s, 2H), 3.82(t, 4H), 2.48(t, 4H), 2.34(s, 3H), 2.0(s, 3H) |
| 12 | DMSO-d₆ | 8.28(s, 1H), 6.18–6.04(br.d, 4H), 2.1(s, 3H) |
| 13 | CDCl₃ | 7.51(d, 1H), 7.18(d, 1H), 4.36–4.22 (br.s, 2H), 3.16(s,6H), 2.0(s, 3H) |
| 14 | DMSOd₆ | 6.10(s, 2H), 6.45(s, 2H), 7.15(d, 1H), 7.30(t, 1H), 7.55(d, 1H) |
| 15 | DMSO-d₆ | 1.70(s, 3H), 5.60(s, 2H), 5.80(s, 2H), 7.15(d, 1H), 7.30(t, 1H), 7.55(d, 1H) |
| 16 | DMSO-d₆ | 3.04(s, 3H, —OMe), 3.76(d, 1H, J12Hz, —C$\underline{H}_2$OMe) 3.85(d, 1H, J12Hz, —OC$\underline{H}_2$OMe), 5.84 (br.s, 2H, —NH₂), 6.05(br.s, 2H, —NH₂), |

TABLE OF ¹H NMR DATA (δ)

| EXAMPLE NO. | SOLVENT | ASSIGNMENT |
|---|---|---|
| | | 7.22(dd, 1H, J7.5, 1.5Hz, 6'-H), 7.38 (dd, 1H, J7.5Hz, 5'-H), 7.6(dd, 1H, J7.5, 1.5Hz, 4'-H) |
| 17 | DMSO-$d_6$ | 7.3–8.0(m, 8H), 6.0–6.1(br.s, 2H), 5.2–5.4(br.s, 2H) |
| 18 | DMSO-$d_6$ | 4.75(2×dd, 2H, J47, 15Hz, —$CH_2$F), 5.95(br.s, 2H, —$NH_2$), 6.15(br.s, 2H, —$NH_2$), 7.25(dd, 1H, J7.5, 1.0Hz, 6'-H), 7.39 (dd, 1H, J7.5Hz), 7.64(dd, 1H, J7.5, 1.0Hz) |
| 19 | DMSO-$d_6$ | 4.43(d, 1H, J11Hz), 4.53(d, 1H, J11Hz), 5.95(br.s, 2H), 6.12(br.s, 2H), 6.7(m, 2H), 6.85(dd, 1H, J7Hz), 7.1-7.4(m, 4H), 7.55(dd, 1H, J7, 1Hz). |
| 20 | DMSO-$d_6$ | 4.4(d, 1H, J12Hz, —$CH_2$OPh), 4.52(d, 1H, J12Hz, —$CH_2$OPh), 5.92(br.s, 2H, —$NH_2$), 6.12(br.s, 2H, —$NH_2$), 6.69(dd, 1H, J7.5, 1.0Hz, 6'-H), 6.85(dd, 1H, J7.5Hz, 5'-H), 7.10–7.35 (m, 5H, —OPh), 7.55(dd, 1H, J7.5, 1.0Hz, 4'-H) |
| 21 | DMSO-$d_6$ | 7.52(s, 1H), 7.15–7.75(m, 3H), 6.02(br.s, 4H, 2×—$NH_2$) |
| 25 | DMSO-$d_6$ | 6.07(s, 2H), 6.25(s, 2H), 7.25(d, 1H), 7.45(d, 1H), 7.63(s, 1H) |
| 26 | DMSO-$d_6$ | 3.88(d, 1H, J11Hz), 4.0(d, 1H, J11Hz), 4.3(s, 2H), 5.9(br.s, 2H), 6.1(br.s, 2H), 7.05–7.2(m, 2H), 7.2–7.35(m, 4H), 7.4(dd, 1H, J8, 2.5Hz), 7.62(d, 1H, J2.5Hz) |
| 28 | DMSO-$d_6$ | 6.25(s, 2H), 6.50(s, 2H), 7.30(s, 1H), 7.40(d, 1H), 7.50(d, 1H) |
| 29 | DMSO-$d_6$ | 5.85(s, 2H), 6.1(s, 2H), 7.25(s, 1H), 7.45(s, 1H), 7.7(s, 1H) |
| 30 | $CDCl_3$ | 7.53–7.12(m, 4H), 4.48–4.30(br.s, 2H), 3.81(t, 4H), 2.46(t, 4H), 2.33(s, 3H), 2.03(s, 3H) |
| 32 | $CDCl_3$ | 7.38(d, 1H), 7.2(dd, 1H), 7.08(d, 1H), 8.2(br.s, 2H) |
| 33 | DMSO-$d_6$ | 7.7(d, 1H), 7.48(dd, 1H), 7.29(d, 1H), 6.45(br.s, 2H), 6.2(br.s, 2H) |
| 34 | $CDCl_3$ | 7.5(d, 1H), 7.35(dd, 1H) 7.18(d, 1H), 5.25(br.s, 2H), 2.44(s, 3H) |
| 35 | $CDCl_3$ | 7.52(d, 1H), 7.32(dd, 1H), 7.21(d, 1H), 5.08(br.s, 2H), 4.66(br.s, 2H), 2.42(s, 3H) |
| 36 | DMSO-$d_6$ | 1.9(s, 3H, 6-$CH_3$), 2.2(s, 3H, N—Me), 2.25–2.40(m, 4H, —N N—), 3.55–3.75 (m, 4H, —N N—), 5.85(2H, br.s, —$NH_2$), 7.2(d, 2H, J1.5Hz, 2', 6'-H), 7.52(dd, 1H, J1.5Hz, 4'-H) |
| 56 | DMSO-$d_6$ | 7.58(dd, 1H). 7.45(dd, 1H), 7.35(d, 1H), 7.24(br.s, 1H), 3.35(br.s, 2H) 3.96(br.s, 2H) |
| 57 | DMSO-$d_6$ | 1.8(s, 3H), 5.8(s, 2H), 5.95(s, 2H), 7.53(s, 1H), 7.92(s, 1H) |
| 58 | DMSO-$d_6$ | 7.78(d, 1H), 7.59(s, 1H), 7.36(d, 1H), 6.60–6.47(br.t, 1H), 6.25–6.03(br.s, 2H), 3.25(q, 2H), 1.1(t, 3H) |

In the foregoing, the signals have been abbreviated as follows: s = singlet; d = doublet; dd = doublet of doublets; t = triplet; q = quadruplet; m = multiplet; br.s = broad singlet; br.t = broad triplet.

Pharmacological Activity

Inhibition of Glutamate Release and Inhibition of Rat Liver DHFR

Compounds of Formula (I) were tested for their effect on veratrine-evoked release of glutamate from rat brain slices according to the protocol described in Epilepsia 27(5): 490–497, 1986. The protocol for testing for inhibition of DHFR activity was a modification of that set out in Biochemical Pharmacology Vol. 20 pp 561–574, 1971.

The results are given in Table 1, the $IC_{50}$ being the concentration of compound to cause 50% inhibition of (a) veratrine-evoked release of glutamate and (b) of DHFR enzyme activity.

TABLE 1

| Compound of Example No. | $IC_{50}(\mu M)$ Glutamate Release (P95 limits) | $IC_{50}(\mu M)$ Rat Liver DHFR (P95 limits) |
|---|---|---|
| 1 | 1.18 (0.50–2.60) | >100 |
| 2 | 0.56 (0.23–1.37) | 33 (27.00–40.00) |
| 3 | 2.15 (0.90–5.10) | >100 |
| 4 | 0.33 (0.196–0.566) | >30 < 100 |
| 5 | 3.50 (1.10–10.40) | ca.100 |
| 6 | 0.70 (0.40–1.50) | 0.51 (0.36–0.73) |
| 7 | <10.00 | >10.0 |

TABLE 1-continued

| Compound of Example No. | IC$_{50}$(μM) Glutamate Release (P95 limits) | IC$_{50}$(μM) Rat Liver DHFR (P95 limits) |
|---|---|---|
| 8 | <10.00 | >10.0 |
| 9 | <10.00 | >100.00 |
| 10 | <10.00 | >100.00 |
| 11 | 4.80 (2.30–10.20) | >100.00 |
| 12 | <10.00 | >100.00 |
| 13 | <10 | >100.00 |
| 14 | 3.1 (2.1–4.6) | >100.00 |
| 15 | 2.7 (1.0–7.2) | 8.7 (5.2-14.7) |
| 16 | 3.2 (1.7–6.1) | >100 |
| 17 | 2.4 (1.00–5.80) | 4.9 (3.90–6.20) |
| 18 | <10.00 | ca.100 |
| 19 | 2.6 (0.80–8.50) | >100.00 |
| 20 | 4.2 (1.20–15.30) | 17.50(9.80–31.40) |
| 21 | 11.5 (4.80–27.60) | 16.01(12.05–21.282) |
| 22 | 2.80 (0.80–9.80) | 23.800(9.00–61.00) |
| 23 | 8.70 (2.60–29.10) | 20.940(9.00–61.00) |
| 24 | 2.10 (0.90–4.80) | 15.10(11.00–20.70) |
| 25 | 4.10 (1.10–15.50) | >100.00 |
| 26 | ca.3.00 | c10.00 |
| 27 | ca.10.00 | >100.00 |
| 28 | 4.6(1.60–13.30) | 46.10(14.30–148.90) |
| 29 | 1.57(0.94–2.62) | 0.53(0.348–0.812) |

Toxtcological Example

The compound of Example 1 has been administered intravenously to groups of six male and six female Wistar rats once daily at dose levels of upto 15 mg/kg/day. The no observsed effect dose was 2.5 mg/kg/day.

The compound of Example 2, has been tested in both rats and dogs. In rats the no observed effect dose was 2.5 mg/kg/day and in dogs, the no observed effect dose was 14 mg/kg/day.

Pharmaceutical Formulation Example

Tablet:

INGREDIENT

| A: Compound of Example 1 | 150 mg ) |
|---|---|
| Lactose | 200 mg ) |
| Maize Starch | 50 mg ) |
| Polyvinylpyrrolidone | 4 mg ) |
| Magnesium Stearate | 4 mg ) |

) = contents per tablet.

The drug was mixed with the lactose and starch and granulated with a solution of the polyvinylpyrrolidone in water. The resultant granules were dried, mixed with magnesium stearate and compressed to give tablets.

B: INJECTION (I)

The salt of the compound of Formula I was dissolved in sterile water for injection.

INTRAVENOUS INJECTION FORMULATION (II)

Active ingredient 0.20 g

Sterile, pyrogen-free phosphate buffer (pH9.0) to 10 ml

The compound of Example I as a salt is dissolved in most of the phosphate buffer at 35°–40° C., then made up to volume and filtered through a sterile micropore filter into sterile 10 ml glass vials (Type 1) which are sealed with sterile closures and overseals.

In the following Examples, the active compound maybe any compound of formula (I) or pharmaceutically acceptable salt thereof.

C: Capsule Formulations

Capsule Formulations A

Formulation A may be prepared by admixing the ingredients and filling two-part hard gelatin capsules with the resulting mixture.

| | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
| | 420 |

Capsule Formulation B

| | mg/capsule |
|---|---|
| (a) Active ingredient | 250 |
| (b) Macrogel 4000 BP | 350 |
| | 600 |

Capsules may be prepared by melting the Macrogel 4000 BP, dispersing the active ingredient in the melt, and filling two-part hard gelatin capsules therewith.

Capsule Formulation B (Controlled Release Capsule)

| | mg/capsule |
|---|---|
| (a) Active ingredient | 250 |
| (b) Microcrystalline Cellulose | 125 |
| (c) Lactose BP | 125 |
| (d) Ethyl Cellulose | 13 |
| | 513 |

The controlled-released capsule formulation may be prepared by extruding mixed ingredients (a) to (c) using an extruder, then spheronising and drying the extrudate. The dried pellets are coated with ethyl cellulose (d) as a controlled-release membrane and filled into two-part hard gelatin capsules.

| Syrup formulation | | |
|---|---|---|
| Active ingredient | | 0.2500 g |
| Sorbitol Solution | | 1.5000 g |
| Glycerol | | 1.0000 g |
| Sodium Benzoate | | 0.0050 g |
| Flavour | | 0.0125 ml |
| Purified Water | q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| Suppository formulation | mg/suppository |
| --- | --- |
| Active ingredient (63 μm)* | 250 |
| Hard Fat, BP (Witepsol H15 - Dynamit Nobel) | 1770 |
| | 2020 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 μm stainless steel screen and, with continuous stirring, allowed to cool to 40° C. At a temperature of 38°–40° C., 2.02 g aliquots of the mixture are filled into suitable plastic moulds and the suppositories allowed to cool to room temperature.

We claim:

1. The method of alleviating cerebral ischaemic damage in a mammal who has had a stroke which comprises administering to said mammal an effective cerebral ischaemic damage-alleviating amount of 4-amino-2-(4-methylpiperazin-1-yl)-5-(2,3,5-trichlorophenyl)pyrimidine or a pharmaceutically acceptable acid addition salt thereof.

2. The method of claim 1 in which the amount administered is 2 to 15 mg/kg of mammal bodyweight.

3. The method of claim 2 in which the said mammal is a human.

4. The method of claim 1 in which an inorganic acid said salt is administered.

5. The method of claim 1 in which an organic acid said salt is administered.

6. The method of claim 1 in which a said salt formed from an acid selected from the group consisting of hydrochloric, hydrobromic, sulphuric, citric, tartaric, phosphoric, lactic, pyruvic, acetic, succinic, fumaric, maleic, oxaloacetic, ethanesulphonic, 2-toluenesulphonic, benzenesulphonic and isethionic acids is administered.

7. The method of claim 1 in which 4-amino-2-(4-methylpiperazin-1-yl)-5-(2,3,5-trichlorophenyl)pyrimidine methanesulphonate is administered.

8. The method of claim 1 in which the 4-amino-2-(4-methylpiperazin-1-yl)-5-(2,3,5-trichlorophenyl)pyrimidine or salt thereof is administered orally.

9. The method of claim 1 in which the 4-amino-2-(4-methylpiperazin-1-yl)-5-(2,3,5-trichlorophenyl)pyrimidine or salt thereof is administered by injection.

10. The method of claim 1 in which the 4-amino-2-(4-methylpiperazin-1-yl)-5-(2,3,5-trichlorophenyl)pyrimidine or salt thereof is administered intravenously.

11. The method of claim 1 in which the said mammal is a human.

12. The method of alleviating cerebral ischaemic damage in a human who has had a stroke which comprises administering to said human a pharmaceutical formulation comprising one or more acceptable carriers and an effective cerebral ischaemic damage-alleviating amount of 4-amino-2-(4-methylpiperazine-1-yl)-5-(2,3,5-trichlorophenyl)pyrimidine or a pharmaceutically acceptable acid addition salt thereof.

* * * * *